US012667721B2

(12) United States Patent
Yu

(10) Patent No.: US 12,667,721 B2
(45) Date of Patent: Jun. 30, 2026

(54) BEAUTY INSTRUMENT

(71) Applicant: Shenzhen GEMO Science and Technology Co., Ltd., Shenzhen (CN)

(72) Inventor: Fei Yu, Shenzhen (CN)

(73) Assignee: Shenzhen GEMO Science and Technology Co., Ltd., Shenzhen (CN)

( * ) Notice: Subject to any disclaimer, the term of this patent is extended or adjusted under 35 U.S.C. 154(b) by 291 days.

(21) Appl. No.: 18/527,184

(22) Filed: Dec. 1, 2023

(65) Prior Publication Data

US 2024/0299740 A1 Sep. 12, 2024

(30) Foreign Application Priority Data

Mar. 7, 2023 (CN) ........................ 202320495316.7

(51) Int. Cl.

| | |
|---|---|
| ***A61N 1/32*** | (2006.01) |
| ***A61F 7/00*** | (2006.01) |
| ***A61F 7/02*** | (2006.01) |
| ***A61N 1/02*** | (2006.01) |
| ***A61N 1/04*** | (2006.01) |
| ***A61N 1/36*** | (2006.01) |
| ***A61N 1/40*** | (2006.01) |

(52) U.S. Cl.

CPC ................ *A61N 1/328* (2013.01); *A61F 7/02* (2013.01); *A61N 1/025* (2013.01); *A61N 1/0452* (2013.01); *A61N 1/0476* (2013.01); *A61N 1/40* (2013.01); *A61F 2007/0087* (2013.01); *A61N 1/3603* (2017.08)

(58) Field of Classification Search

None

See application file for complete search history.

(56) References Cited

U.S. PATENT DOCUMENTS

2016/0089537 A1 3/2016 Yamazaki

FOREIGN PATENT DOCUMENTS

| | | | |
|---|---|---|---|
| CN | 210871255 U | | 6/2020 |
| CN | 211097038 U | | 7/2020 |
| CN | 211273147 U | | 8/2020 |
| CN | 212522725 U | | 2/2021 |
| CN | 212941026 U | | 4/2021 |
| CN | 214839323 U | | 11/2021 |
| CN | 113813507 A | | 12/2021 |
| CN | 113874069 A | | 12/2021 |
| CN | 215653421 U | * | 1/2022 |

(Continued)

*Primary Examiner* — Michael W Kahelin

(74) *Attorney, Agent, or Firm* — ScienBiziP, P.C.

(57) ABSTRACT

This application discloses a beauty instrument which includes: a housing, where the housing includes a working head; and an electrical stimulation component which includes an EMS stimulation circuit, an RF radio frequency circuit, and a ring electrode, a first group of electrodes, and a second group of electrodes that are all disposed on the working head, the ring electrode is separately connected to the EMS stimulation circuit and the RF radio frequency circuit, the first group of electrodes includes a plurality of first electrodes that are distributed at intervals around the ring electrode, the plurality of first electrodes are all connected to the RF radio frequency circuit and/or connected to the EMS stimulation circuit, the second group of electrodes includes a plurality of second electrodes that are all connected to the EMS stimulation circuit.

13 Claims, 29 Drawing Sheets

(56) References Cited

FOREIGN PATENT DOCUMENTS

| | | | | |
|---|---|---|---|---|
| CN | 216497023 | U | | 5/2022 |
| CN | 2016497023 | U | * | 5/2022 |
| CN | 218280325 | U | | 1/2023 |
| CN | 218474790 | U | | 2/2023 |
| JP | 2021027969 | A | | 2/2021 |
| KR | 20240036349 | | * | 3/2024 |
| WO | WO2021020270 | A1 | | 2/2021 |

* cited by examiner

BEAUTY INSTRUMENT

CROSS-REFERENCE TO RELATED APPLICATIONS

This application is based on Chinese Patent Application No. 2023204953167, filed on Mar. 7, 2023 and entitled "BEAUTY INSTRUMENT", and claims priority to this Chinese Patent Application, which is incorporated herein by reference in its entirety.

TECHNICAL FIELD

This application relates to the field of electronic device technologies, and in particular, to a beauty instrument.

BACKGROUND

In a related technology, a radio frequency (RF) technology is generally used in some beauty instruments. Radio frequency is an electromagnetic wave with energy and a penetration capability. When the beauty instrument is used, the radio frequency penetrates the epidermis of a user and reaches the dermis thereof, and electromagnetic energy is converted into heat energy, so that the dermis is slightly and controllably burned, to damage the collagen (slightly aged) existing in the dermis, thereby stimulating a repair mechanism of the skin, and producing new collagen to replace the collagen damaged by the heat energy.

However, in the related technology, only RF radio frequency beauty treatment is used. As a result, a beauty method is single and user experience is poor.

SUMMARY

This application mainly provides a beauty instrument, to resolve a problem of a single beauty method of the beauty instrument.

To resolve the foregoing technical problem, a technical solution used in this application is to provide a beauty instrument. The beauty instrument includes: a housing, where the housing includes a working head; and an electrical stimulation component, where the electrical stimulation component includes an EMS stimulation circuit, an RF radio frequency circuit, and a ring electrode, a first group of electrodes, and a second group of electrodes that are all disposed on the working head, the ring electrode is separately connected to the EMS stimulation circuit and the RF radio frequency circuit, the first group of electrodes includes a plurality of first electrodes, the plurality of first electrodes are all connected to the RF radio frequency circuit and/or connected to the EMS stimulation circuit, the plurality of first electrodes are distributed at intervals around the ring electrode, the second group of electrodes includes a plurality of second electrodes, the plurality of second electrodes are all connected to the EMS stimulation circuit, and the plurality of second electrodes are distributed at intervals around the first group of electrodes.

Beneficial effects of this application are as follows: Different from the conventional technology, this application discloses a beauty instrument, and the beauty instrument includes a housing with a working head and an electrical stimulation component, where the electrical stimulation component includes an EMS stimulation circuit, an RF radio frequency circuit, and a ring electrode, a first group of electrodes, and a second group of electrodes that are all disposed on the working head, and the ring electrode is separately connected to the EMS stimulation circuit and the RF radio frequency circuit. Therefore, the beauty instrument in this application has a radio frequency function that may focus energy on the dermis to stimulate regeneration of the collagen and tighten the skin, and further has an EMS microcurrent stimulation function that stimulates the muscle and lymph by using a weak current, to contract the muscle, so as to reduce edema and lift and tighten the skin. When the beauty instrument is used with skin care products and targeted anti-aging essence, an EMS microcurrent can also open a surface channel of the skin to accelerate nutrient absorption.

BRIEF DESCRIPTION OF DRAWINGS

To describe the technical solutions in the embodiments of this application or the conventional technology more clearly, the following briefly describes the accompanying drawings required for describing the embodiments or the conventional technology. Clearly, the accompanying drawings described below are only some embodiments of this application. A person of ordinary skill in the art may further derive other accompanying drawings based on these accompanying drawings without creative efforts.

Figure 1:
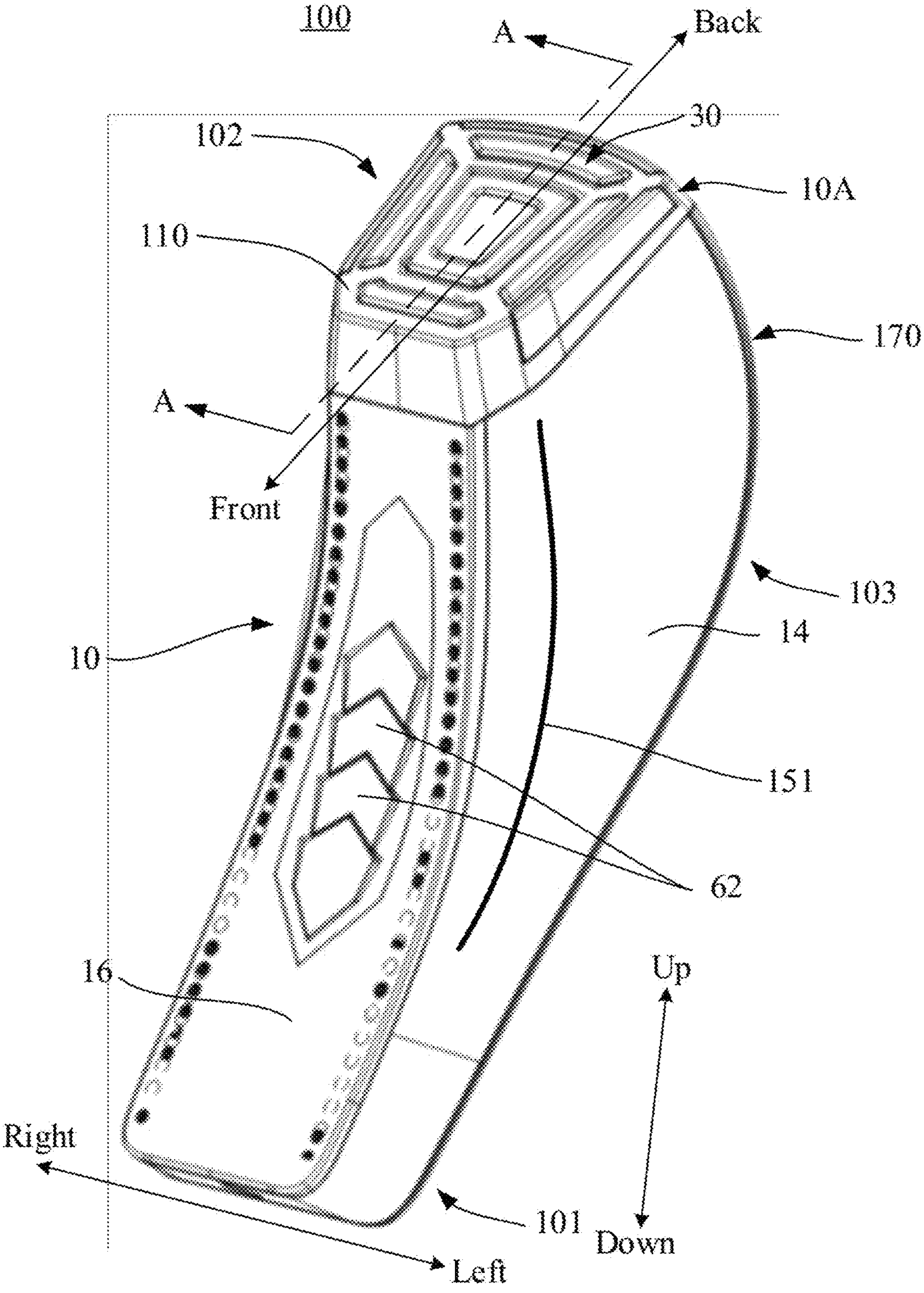
FIG. 1 is a schematic diagram of a three-dimensional structure of a beauty instrument according to some embodiments of this application.

Reference numerals: 100—beauty instrument, 10—housing, 10A—working head, 10B—housing body, 10C—opening, 10D—handheld segment, 10E—expansion segment, 10F—connection panel, 10G—connection pillar, 10H—joining wall, 10K—inner side surface, 101—tail, 102—head, 103—middle part, 11—top panel, 110—working surface, 111—front side edge, 112—rear side edge, 11A—annular side panel, 11B—side wall, 11C—limiting ring protrusion, 12—front-side protection panel, 121—first handheld part, 122—first expansion part, 123—mounting pillar. 13—inner housing back cover, 131—second handheld part, 132—second expansion part, 133—extension part, 134—mounting hole, 14—left side panel, 141—convex part, 142—concave part, 15—right side panel, 151—convex part. 152—concave part, 16—font cover, 17—back cover, 170—rear side surface, 171—curved surface part, 172—palm holding part, 173—finger touching part, 174—recessed part, 175—connection hole, 18—left support panel, 19—right support panel, 20—handle, 21—connection pillar, 21A—first connection pillar. 21B—second connection pillar, 211—first end, 2111—connection component, 2112—connection protrusion pillar, 212—second end, 213—second groove, 214—reinforcement rib, 215—first trigger part, 216—second trigger part, 22—blocking part, 221—first groove, 23—limiting space, 24—first function button, 241—on/off button, 242—function selection button, 26—second function button, 27—surface, 30—electrode, 31—center electrode, 32—upper electrode. 33—right electrode, 34—lower electrode, 35—left electrode, 36—upper edge electrode, 37—left edge electrode, 38—right edge electrode, 39—electrode circuit board, 40—heat dissipation member, 41—heat dissipation body, 410—support pillar, 411—through hole. 42—mounting protrusion part, 420—mounting surface, 421—mounting panel, 422—barrier wall, 423—accommodation space, 424—connection hole, 425—side surface, 43—hollow part, 431—first hollow part, 432—second hollow part, 44—connection part, 441—first edge, 442—second edge, 443—third edge, 45—first gap, 51—cold compress member, 511—contact surface, 512—conduction surface, 52—refrigeration member, 53—first thermally conductive silicone, 54—second thermally conductive silicone, 61—button circuit board. 62—button, 63—button light guide member, 64—decorative button panel, 71—main control circuit board, 81—charging interface, A1—length direction, A2—width direction. A3—thickness direction, 113—fastening pillar, 116—fastening protrusion part, 104—receiving slot, 105—rear panel, 106—left panel, 107—right panel, 108—front panel, 109—accommodation slot, 11D—front enclosure panel, 11E—rear enclosure panel, 11F—left enclosure panel, 11G—right enclosure panel, 104A—connection through hole, 114—connection groove, 115—accommodation groove, 301—connection protrusion part, 302—positioning protrusion pillar. 72—EMS stimulation circuit, 73—RF radio frequency circuit, B1—first arrow direction, and B2—second arrow direction.

DETAILED DESCRIPTION OF THE EMBODIMENTS

The following clearly describes the technical solutions in embodiments of this application with reference to the accompanying drawings in the embodiments of this application. Clearly, the described embodiments are merely some but not all of embodiments of this application. All other embodiments obtained by a person of ordinary skill in the art based on embodiments of this application without creative efforts shall fall within the protection scope of this application.

The terms "first", "second", and "third" in the embodiments of this application are used only for a purpose of description, and shall not be understood as an indication or implication of relative importance or implicit indication of a quantity of indicated technical features. Therefore, features limited by "first", "second", and "third" may explicitly or implicitly include at least one such feature. In the description of this application, "a plurality of" means at least two, for example, two or three, unless otherwise specifically limited. In addition, the terms "include", "have", and any variant thereof are intended to cover non-exclusive inclusion. For example, a process, method, system, product, or device that includes a series of steps or units is not limited to a listed step or unit, but optionally further includes an unlisted step or unit, or optionally further includes another step or unit inherent to the process, method, product, or device.

Referring to the "embodiments" in this application means that a particular feature, structure, or characteristic described with reference to the embodiments may be included in at least one embodiment of this application. Occurrence of the phrase at various locations in this specification does not necessarily refer to a same embodiment, and does not refer to a separate or alternative embodiment mutually exclusive with another embodiment. A person skilled in the art explicitly and implicitly understands that the embodiments described in this application may be combined with other embodiments.

It should be specifically noted that, for ease of explanation of this application, in this application, some features in this application are named in conjunction with an orientation, and some features such as a front side panel, a rear side panel, a left panel, a right panel, and an upper end are limited in terms of description. However, this is not intended to limit this application. A person skilled in the art should be aware that, when a posture of placing/holding the beauty instrument in this application changes, a corresponding orientation also changes.

Figure 4:
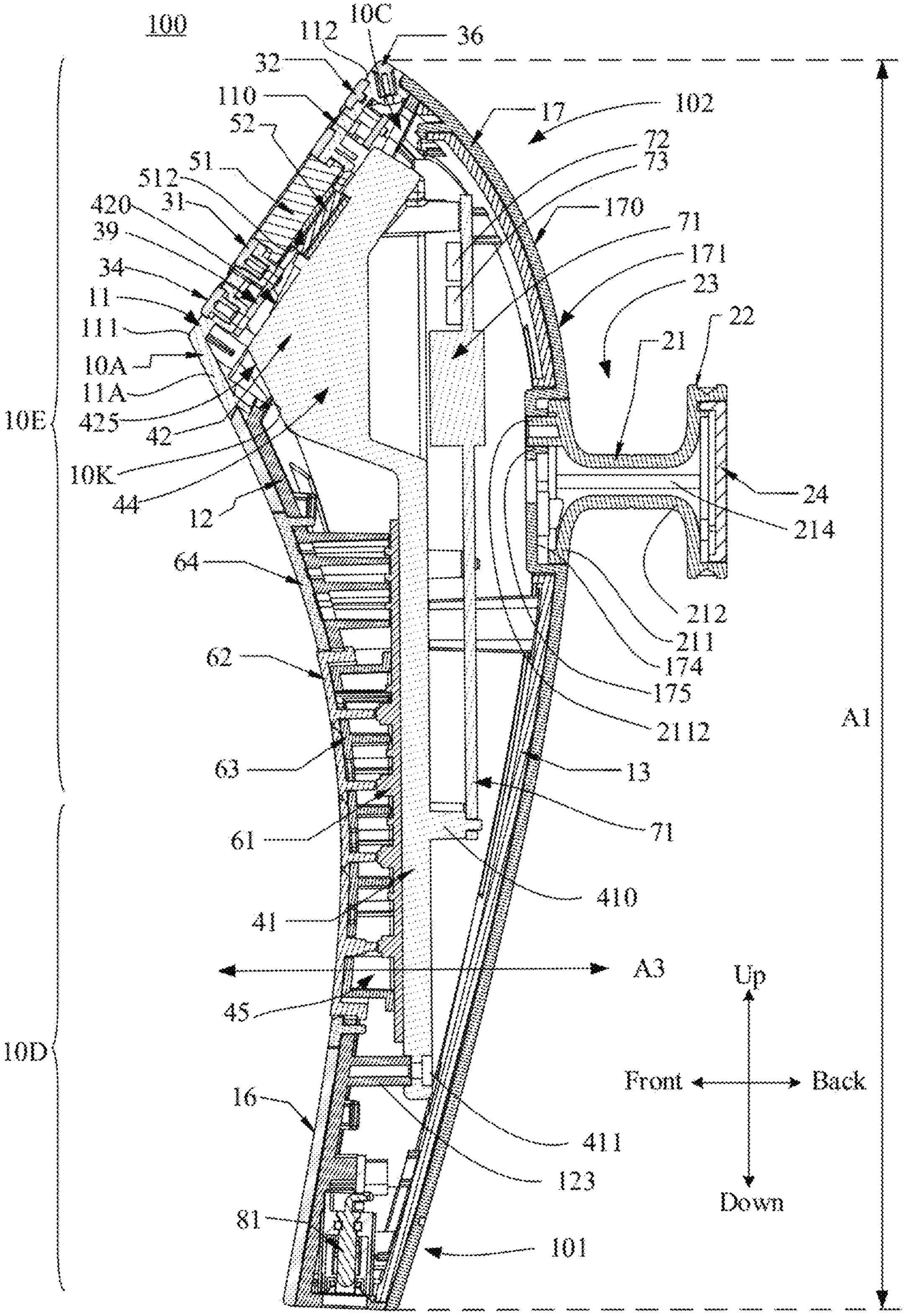
FIG. 4 is a schematic sectional view of the beauty instrument shown in FIG. 1 along A-A.

For ease of understanding, the orientation is limited with reference to FIG. 1 and FIG. 4 in this application. In a posture shown in FIG. 1, a working surface 110 is configured to be attached to to-be-treated skin (for example, facial skin), so that an electrode 30 is in contact with the skin. In this case, an end at which the electrode is located may be defined as an upper end, and the other end is a lower end. A side that is of the beauty instrument and that faces the human body is a front side, and a side away from the human body is a rear side. Based on this, a front side panel, a rear side panel, a left side panel, and a right side panel are defined.

It should also be noted that, in this application, sometimes for ease of description, a front-back direction is also referred to as a thickness direction of a housing, a left-right direction is referred to as a width direction of the housing, and a top-bottom direction is referred to as a length direction.

Figure 2:
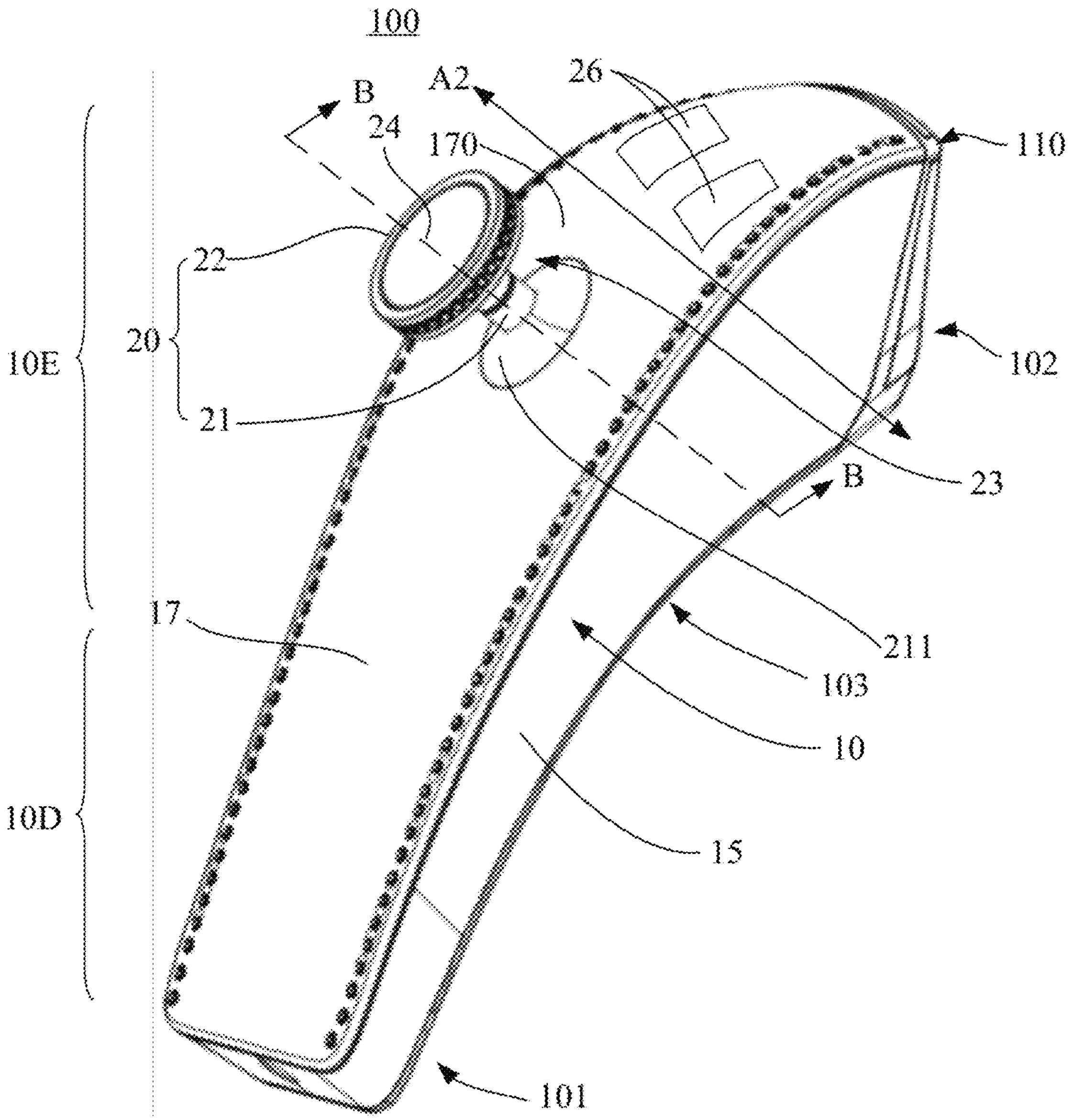
FIG. 2 is a schematic diagram of another three-dimensional structure of the beauty instrument shown in FIG. 1.
Figure 3:
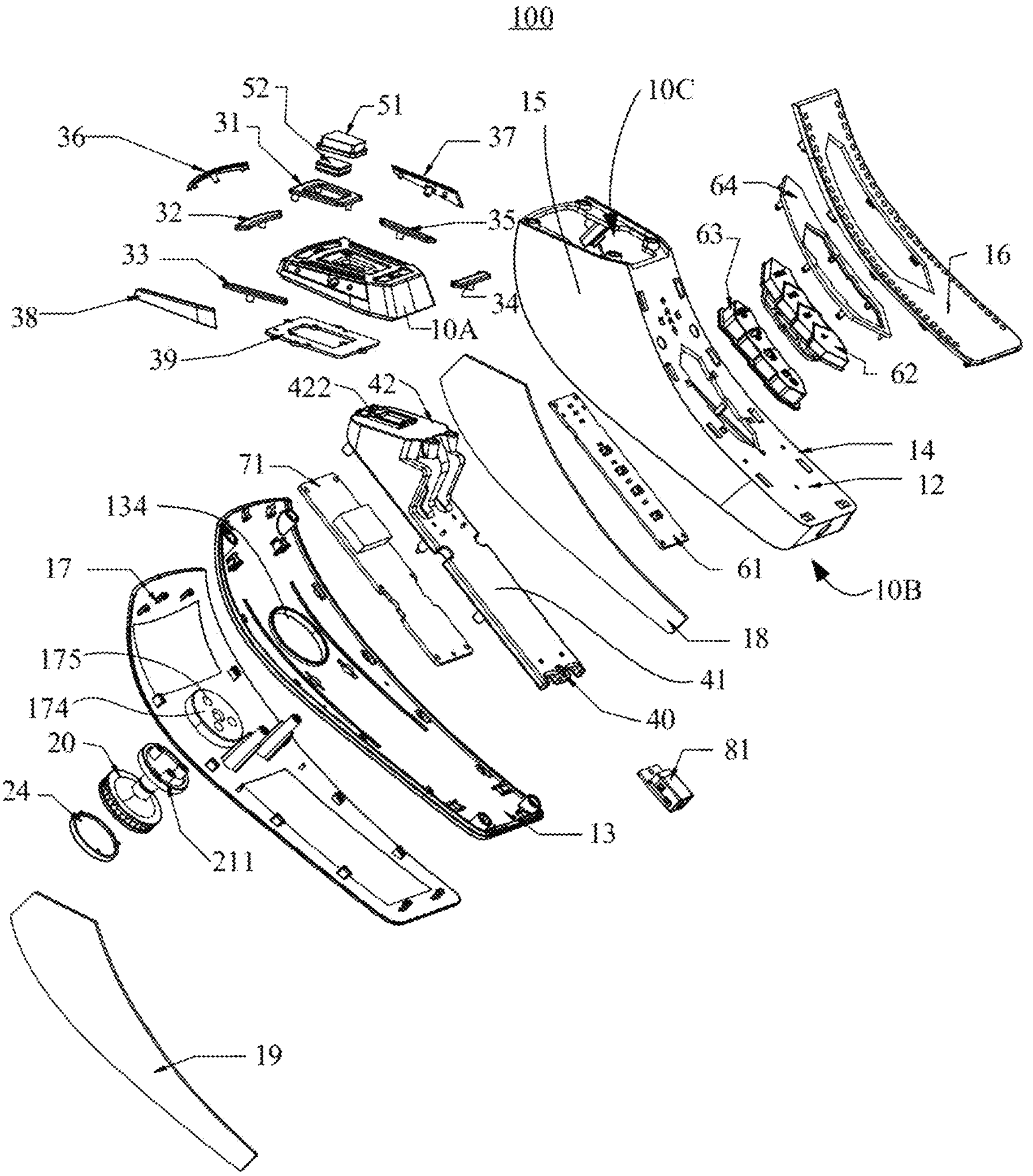
FIG. 3 is a schematic diagram of a three-dimensional exploded structure of the beauty instrument shown in FIG. 1.
Figure 5:
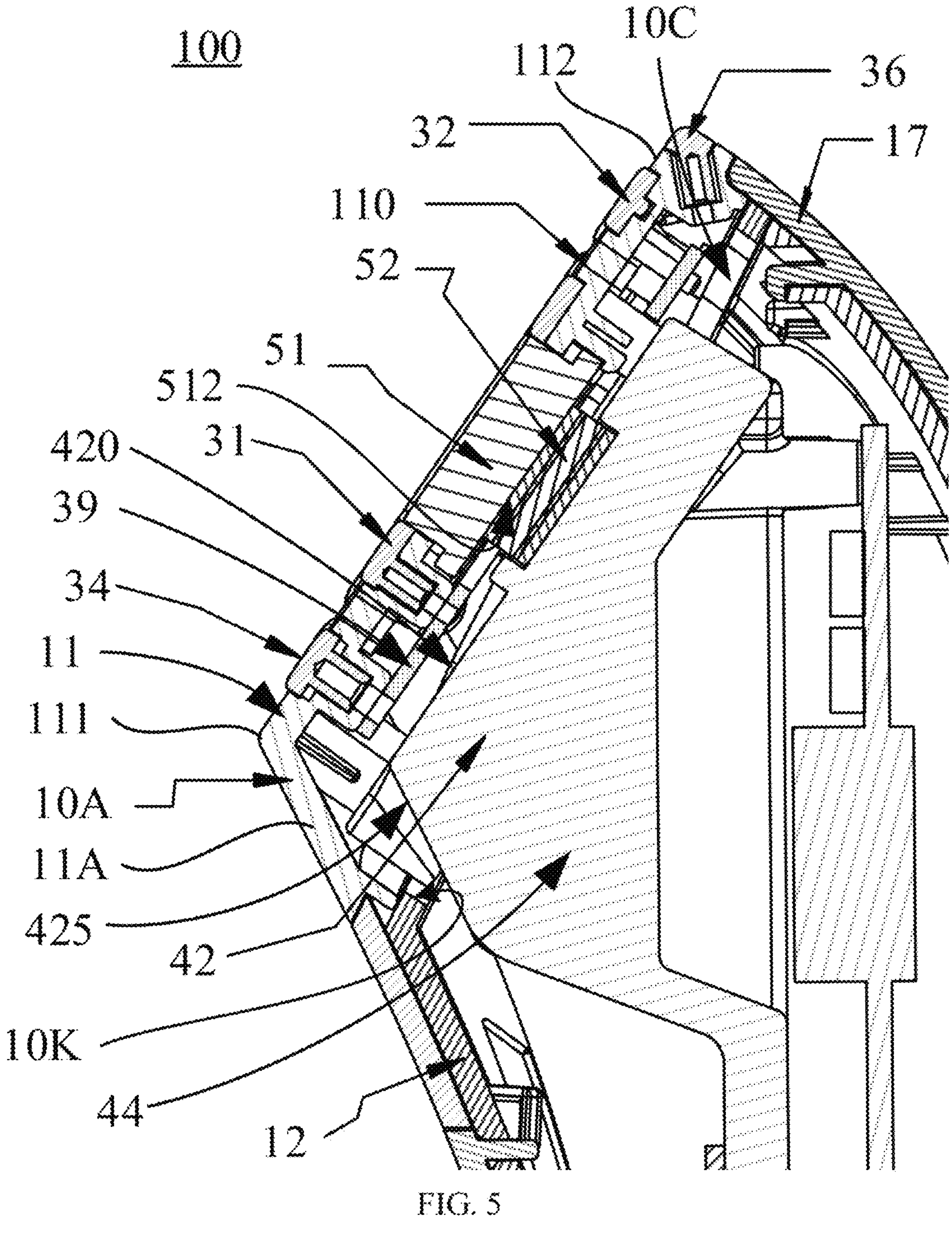
FIG. 5 is a partially enlarged schematic diagram of the beauty instrument shown in FIG. 4.

FIG. 1 and FIG. 2 are two schematic diagrams of a three-dimensional structure of a beauty instrument according to some embodiments of this application, FIG. 3 is a schematic diagram of a three-dimensional exploded structure of the beauty instrument shown in FIG. 1, FIG. 4 is a schematic sectional view of the beauty instrument shown in FIG. 1 along A-A, and FIG. 5 is a partially enlarged schematic diagram of the beauty instrument shown in FIG. 4. This application discloses a beauty instrument 100, where the beauty instrument 100 includes a housing 10, an electrode 30, and a heat dissipation member 40. The housing 10 includes a working head 10A and a housing body 10B, and the working head 10A is combined with the housing body 10B. The housing 10 is configured to provide structural support and mounting space. The working head 10A may also be referred to as a head cover.

The housing body 10B has an opening 10C at one end, the electrode 30 is mounted on the working head 10A, the heat dissipation member 40 is mounted in the housing body 10B, the working head 10A is disposed at the opening 10C of the housing body 10B, and the working head 10A is connected to the heat dissipation member 40.

Further, the heat dissipation member 40 may include a heat dissipation body 41 extending in a length direction A1 of the housing 10 and a mounting protrusion part 42 protruding towards a first side of the heat dissipation body 41. The mounting protrusion part 42 is located in the opening 10C of the housing body 10B, and the working head 10A is connected to the mounting protrusion part 42. The heat dissipation body 41 may be in a plate shape as a whole.

The electrode 30 may be connected to a pulse generation circuit. In this way, when the electrode 30 is in contact with the skin, the pulse generation circuit generates an electrical/magnetic pulse, to perform care such as maintenance on the skin. The electrode 30 may include an RF electrode, and an RF circuit that cooperates with the RF electrode in the electrode 30 may be disposed in the housing 10.

Optionally, the electrode 30 may be made of a 18K gold-plated material, to enhance energy convergence.

Generally, a plurality of electrodes 30 are disposed. For example, an RF electrode may be included, to penetrate into the skin, activate the collagen, lift and tighten the skin, brighten the skin, and reduce wrinkles. An EMS electrode may also be included to vibrate the muscle, so as to implement lifting and shaping.

In this embodiment, the length direction A1 is also a direction of the housing body 10B from one end with an opening to the other end. It is noted herein that, as shown in FIG. 4, when the beauty instrument 100 is upright, the length direction A1 is also a height direction.

In the beauty instrument 100 in the foregoing embodiment, the heat dissipation member 40 is disposed, so that heat generated when an electronic component on the working head 10A works can be dissipated by using the heat dissipation member 40, thereby reducing a temperature of the working head 10A.

In addition, the working head 10A is directly connected to the heat dissipation member 40, so that the working head 10A can be fastened by using the heat dissipation member 40, or the heat dissipation member 40 can be fastened by using the working head 10A. In this way, a component for fastening the working head 10A and/or the heat dissipation member 40 may be reduced, so that an internal structure of the housing 10 can be simplified.

In addition, the working head 10A may be closer to the heat dissipation member 40, to facilitate heat dissipation.

Moreover, in this embodiment, the heat dissipation member 40 may support the working head 10A.

To facilitate description of the technical effects of this application, this application further provides a structure for mounting a head cover and a housing body in a related technology. In this related technology, the head cover is mounted at an opening of the housing body, but a connection skeleton is further disposed between the head cover and the housing body, the connection skeleton is connected to the housing body, a heat dissipation member is mounted on the connection skeleton, and the head cover covers the connection skeleton. However, in this case, a structure at the opening of the housing body is complex.

In some embodiments, as shown in FIG. 1, FIG. 2, FIG. 4, and FIG. 6, FIG. 6 is a schematic diagram of a three-dimensional structure of a heat dissipation member 40 according to this application. The working head 10A has a top panel 11 inclined relative to the length direction A1, the top panel 11 has a working surface 110, and the electrode 30 is exposed to the working surface 110. The top panel 11 is connected to the mounting protrusion part 42. The top panel 11 and the working surface 110 thereof may be in a trapezoid shape or substantially in a trapezoid shape. The top panel 11 is connected to the mounting protrusion part 42, to help dispose a connection structure, and improve connection convenience.

The mounting protrusion part 42 has a mounting surface 420 inclined relative to the length direction A1, the mounting surface 420 faces the top panel 11, and the top panel 11 is connected to the mounting surface 420.

In some embodiments, as shown in FIG. 1, FIG. 2, and FIG. 4 to FIG. 6, the working head 10A and the mounting protrusion part 42 may be mounted and fastened by using a fastener such as a screw. For example, the fastener may be connected to the working head 10A after passing through the mounting protrusion part 42.

In some embodiments, as shown in FIG. 1, FIG. 2, and FIG. 4 to FIG. 6, the working surface 110 is a surface that faces and is close to or is even attached to the skin of a user during use of the beauty instrument 100.

The mounting surface 420 may be substantially parallel to the working surface 110. Through such disposition, an area of the working surface 110 may be large, to help mount the working head 10A on the mounting protrusion part 42.

In some embodiments, with reference to FIG. 3 to FIG. 5, the mounting surface 420 is at least partially configured to protrude from the opening 10C. In other words, the mounting protrusion part 42 is inserted into the opening 10C, so that the mounting surface 420 protrudes from the opening 10C.

In this manner, the mounting surface 420 may be closer to the working head 10A, to facilitate connection and mounting between the mounting protrusion part 42 and the working head 10A. In addition, when the beauty instrument 100 includes a cold compress member 51, the protruding mounting surface 420 is thermally conductively connected to the cold compress member 51 more easily.

Figure 6:
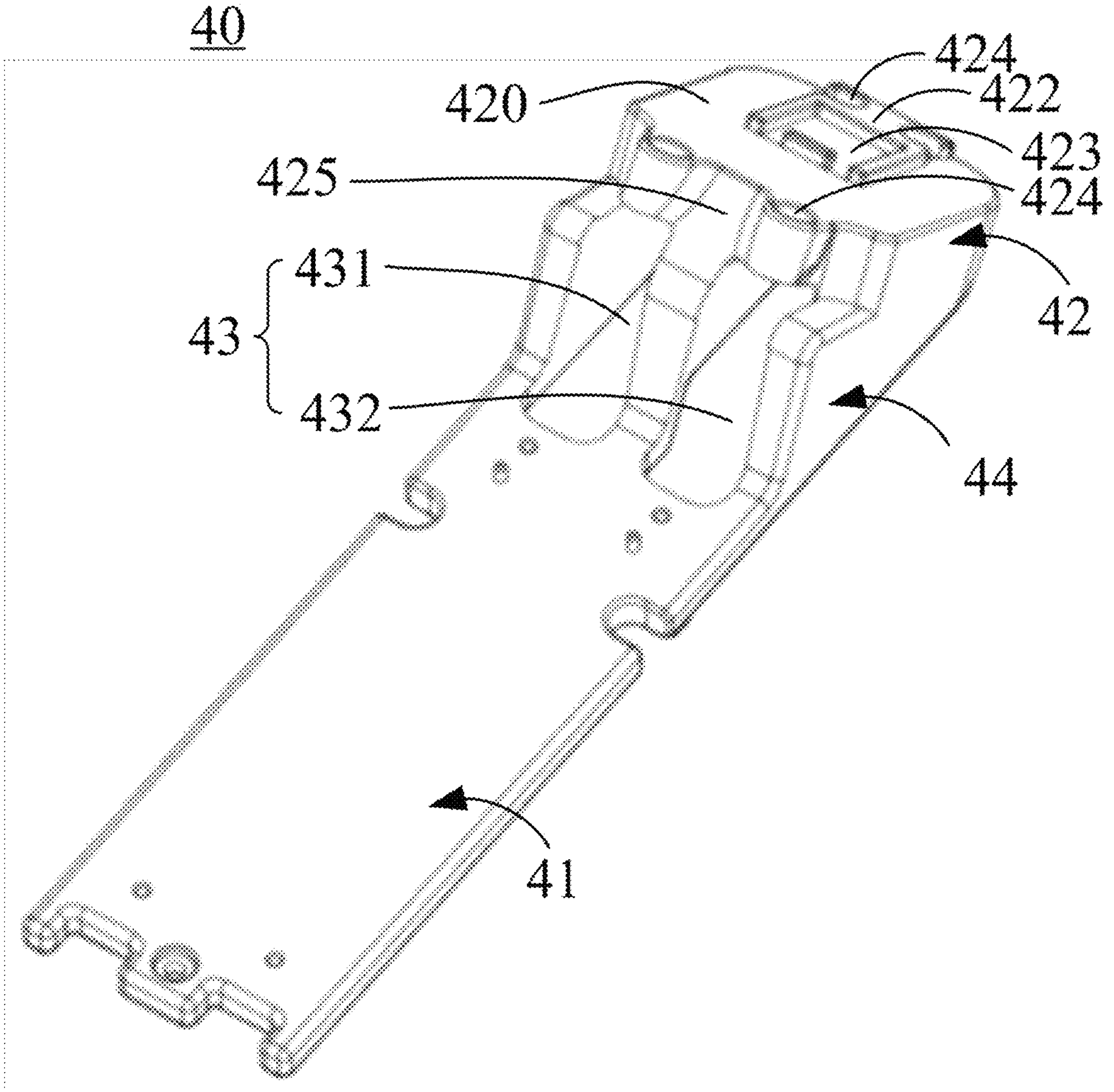
FIG. 6 is a schematic diagram of a three-dimensional structure of a heat dissipation member of a beauty instrument according to some embodiments of this application.

In some embodiments, with reference to FIG. 4 to FIG. 6, the mounting protrusion part 42 has a side surface 425 inclined to the mounting surface 420. The side surface 425 faces an inner side surface 10K of the opening 10C, and there is a gap between the side surface 425 and the inner side surface 10K.

Because the working head 10A needs to be connected and fastened to the mounting protrusion part 42, the gap can be formed to prevent the mounting protrusion part 42 from interfering with the opening 10C of the housing body 10B when the mounting protrusion part 42 is mounted in the beauty instrument 100.

In the embodiments shown in FIG. 4 to FIG. 6, the side surface 425 includes a side surface of a third edge of a connection part 44 and a side surface of a mounting panel 421. The two side surfaces may be on a same plane, or may be on different planes. There is a gap between the side surface of the mounting panel 421 and the inner side surface 10K.

Figure 7:
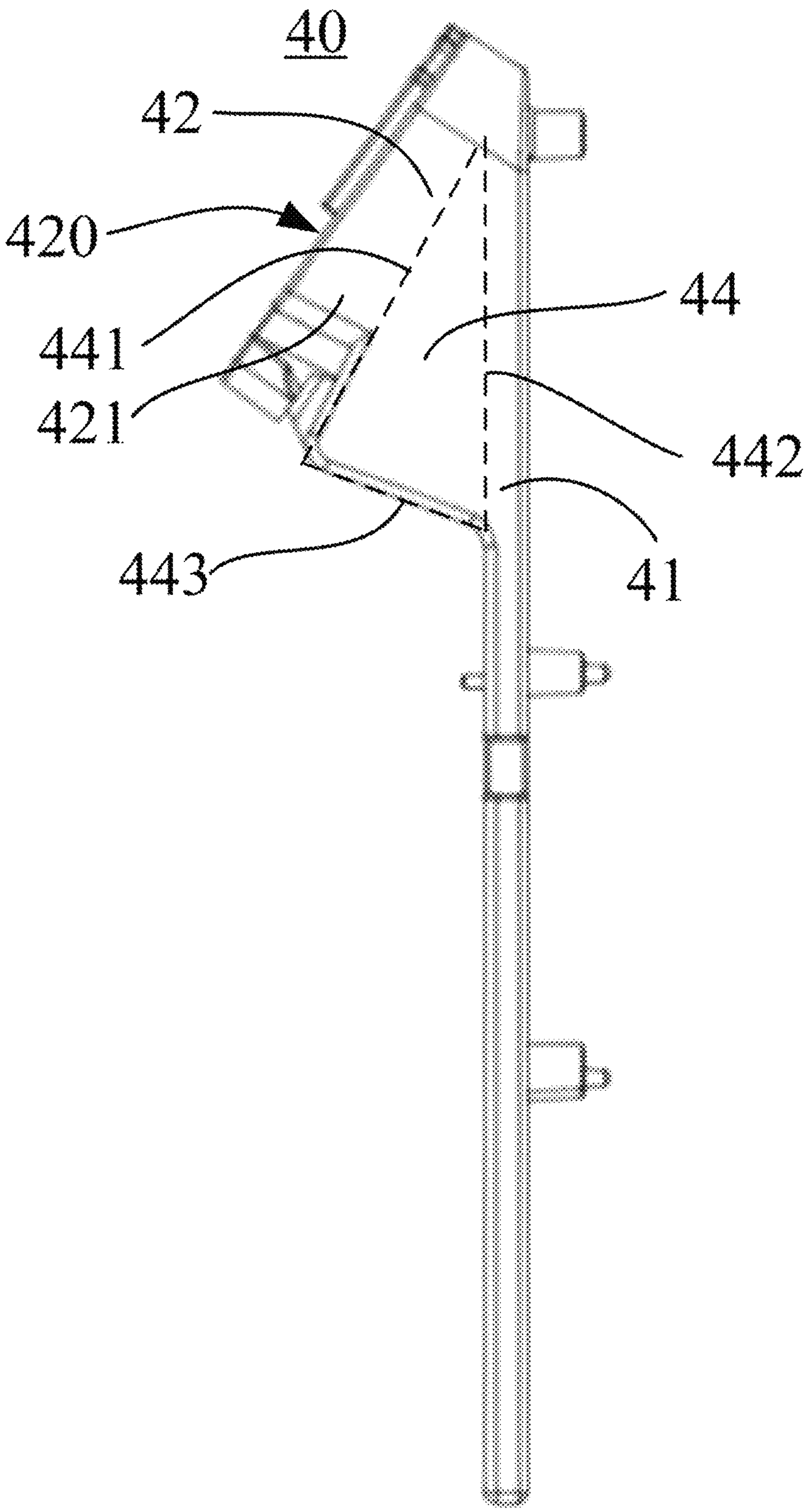
FIG. 7 is a schematic diagram of a side surface of a heat dissipation member of a beauty instrument according to some embodiments of this application.

In some embodiments, as shown in FIG. 6 and FIG. 7, FIG. 7 is a schematic diagram of aside surface of a heat dissipation member according to this application. An included angle between the mounting surface 420 and an extension direction of the heat dissipation body 41 is less than or equal to 40 degrees, for example, may be 40 degrees, 25 degrees, 20 degrees, 18 degrees, or 10 degrees. Therefore, when the included angle between the mounting surface 420 and the heat dissipation body 41 is set to be less than or equal to 40 degrees, the included angle can be adapted to inclined arrangement of the working surface 110 of the working head 10A, so that the working surface 110 has a large area.

Figure 8:
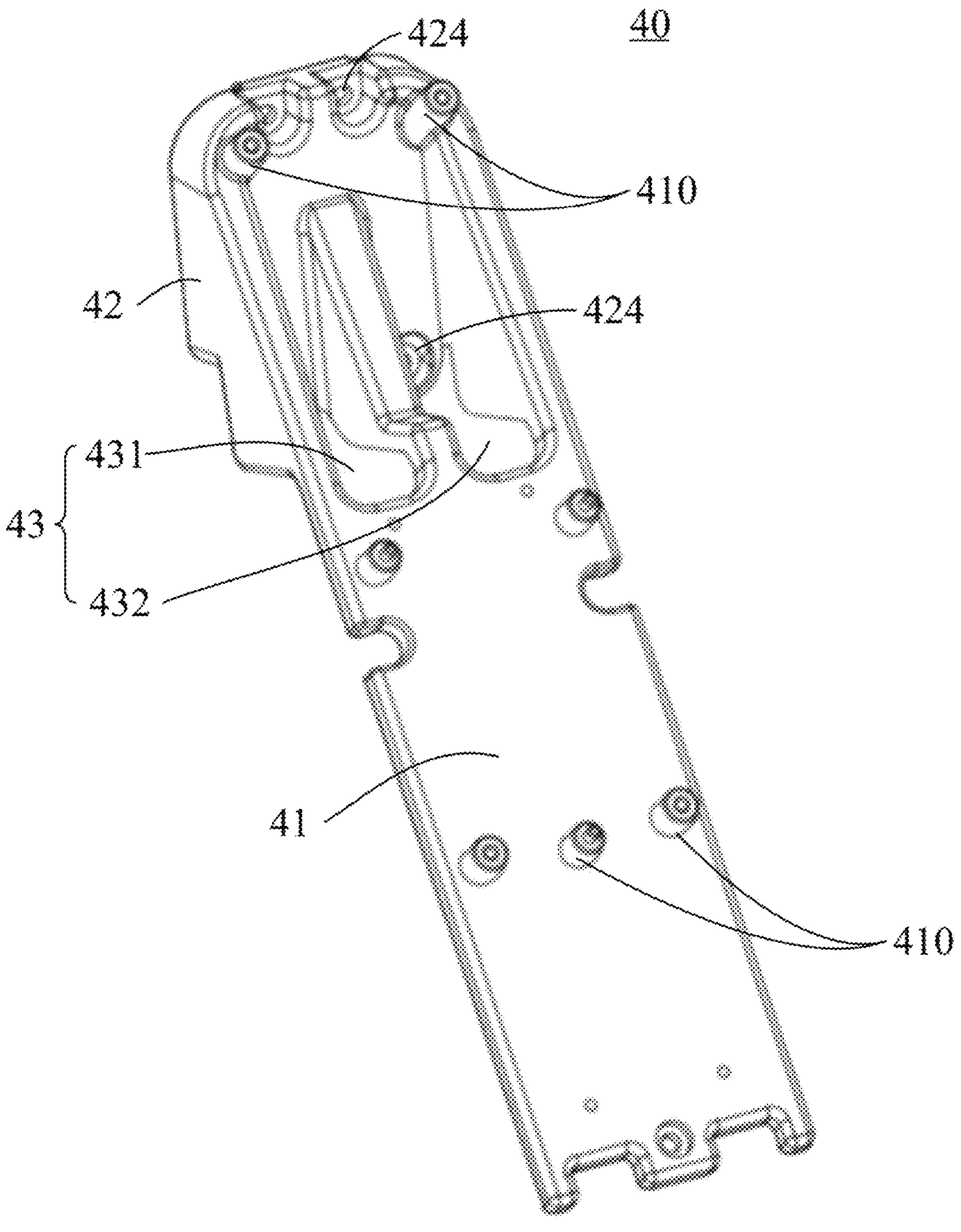
FIG. 8 is a schematic diagram of another three-dimensional structure of a heat dissipation member of a beauty instrument according to some embodiments of this application.

In some embodiments, as shown in FIG. 6 and FIG. 8, FIG. 8 is a schematic diagram of another three-dimensional structure of a heat dissipation member according to some embodiments of this application. The heat dissipation member 40 includes a hollow part 43, and the hollow part 43 is located in the mounting protrusion part 42 and/or the heat dissipation body 41. The hollow part 43 may be a structure such as a notch, a recess, or a through hole that is formed in the heat dissipation member 40. Therefore, the hollow part 43 is disposed on the mounting protrusion part 42, so that a heat dissipation area can be increased, and a quantity of used materials can be reduced.

In some embodiments, as shown in FIG. 6 and FIG. 8, the hollow part 43 penetrates the side surface 425 and a side surface of a second side of the heat dissipation body 41. The hollow part 43 is disposed in this manner, so that while a heat dissipation area is increased, it is convenient for demolding when the heat dissipation member 40 is manufactured.

In some embodiments, with reference to FIG. 3 to FIG. 5, the beauty instrument further includes a cold compress assembly. The cold compress assembly includes a cold compress member 51 mounted on the top panel 11 and a refrigeration member 52 disposed on a side surface of the cold compress member 51, and the refrigeration member 52 is thermally conductively connected to the heat dissipation member 40.

In some embodiments, as shown in FIG. 2 to FIG. 5 and FIG. 9, FIG. 9 is an enlarged exploded schematic diagram of a head assembly of a beauty instrument according to some embodiments of this application. The cold compress member 51 has a contact surface 511 and a conduction surface 512. The contact surface 511 is configured to be in contact with a skin part. A refrigeration side of the refrigeration member 52 is thermally coupled to the conduction surface 512 of the cold compress member 51, to cool the cold compress member 51. The heat dissipation member 40 is thermally coupled to a heating side of the refrigeration member 52, to dissipate heat for the refrigeration member 52. The contact surface 511 and the conduction surface 512 may be opposite to each other. To facilitate thermal coupling, first thermally conductive silicone 53 may be disposed between the refrigeration member 52 and the conduction surface 512, and second thermally conductive silicone 54 may be disposed between the refrigeration member 52 and the mounting protrusion part 42. It is noted herein that the head assembly may include the working head 10A and various components mounted thereon, such as the cold compress member 51, the refrigeration member 52, the electrode 30, and an electrode circuit board 39.

In some embodiments, as shown in FIG. 2 to FIG. 5 and FIG. 9, the cold compress member 51 is a transparent crystal, the transparent crystal is mounted on the working head 10A, the contact surface 511 is exposed to the working head 10A, the conduction surface 512 is opposite to the contact surface 511, and the refrigeration member 52 is disposed on a side that is of the conduction surface 512 and that is away from the contact surface 511.

When the beauty instrument 100 works, the electrode 30 discharges, for example, generates radio frequency or a microcurrent.

During radio frequency beauty treatment, the electrode 30 includes an RF electrode, and may emit an RF radio frequency wave by using the RF electrode. The RF radio frequency wave directly penetrates into deep tissues (such as the dermis) of the skin, to heat fat cells and collagen tissues by using generated high heat energy, so as to stimulate regeneration of the skin collagen and achieve a beauty effect. However, a continuous high temperature may also cause discomfort to the human body. In this application, the refrigeration member 52 can reduce a temperature of the cold compress member 51, so that the cold compress member 51 performs cold compress on a skin part, thereby reducing discomfort of the skin. In this way, the dermis can be heated, the collagen can be activated, and the epidermis layer can be cooled, to implement an icy sensation.

In some embodiments, as shown in FIG. 3 to FIG. 6, a barrier wall 422 is convexly disposed on a side that is of the mounting protrusion part 42 and that faces the cold compress member 51 such as a transparent crystal, the barrier wall 422 surrounds accommodation space 423, and the accommodation space 423 is configured to accommodate the refrigeration member 52. Further, the bottom of the accommodation space 423 may be flush with the mounting surface 420. The barrier wall 422 is disposed, so that the refrigeration member 52 can be positioned. Therefore, in an assembly process, the refrigeration member 52 is first mounted in the accommodation space 423 of the mounting protrusion part 42, and then the mounting protrusion part 42 is connected to and mounted on the working head 10A. When the second thermally conductive silicone 54 is used, the second thermally conductive silicone 54 may be disposed in the accommodation space 423, so that the second thermally conductive silicone 54 is in direct contact with the bottom of the accommodation space 423, and then the refrigeration member 52 is disposed on the second thermally conductive silicone 54. The refrigeration side of the refrigeration member 52 may be flush with the barrier wall 422 or higher than the barrier wall 422. The barrier wall 422 may be of a square frame structure to limit the refrigeration member 52 on four sides. In addition, the barrier wall 422 may be provided with a notch, to allow a wire connected to the refrigeration member 52 to pass through.

In some embodiments, as shown in FIG. 6 to FIG. 8, the heat dissipation member 40 may be made of a material having heat dissipation performance such as copper or aluminum. When the material of the heat dissipation member 40 is copper or aluminum, the heat dissipation member 40 has good thermal conductivity, so that heat of the refrigeration member 52 can be effectively dissipated by using the heat dissipation member 40. In addition, the material used to manufacture the heat dissipation member 40 is common and inexpensive, thereby effectively reducing production costs of the heat dissipation member 40.

In some embodiments, as shown in FIG. 3 and FIG. 4, the beauty instrument 100 may further include a button circuit board 61 and a main control circuit board 71. The main control circuit board 71 is disposed on the second side of the heat dissipation body 41, and the button circuit board 61 is disposed on the first side of the heat dissipation body 41. The button circuit board 61 and the main control circuit board 71 are respectively disposed on two sides of the heat dissipation body 41, so that components in the beauty instrument 100 can be properly laid out, and the button circuit board 61 and the main control circuit board 71 can be supported by using the heat dissipation member 40.

Further, as shown in FIG. 3, the beauty instrument 100 may further include a button 62 connected to the button circuit board 61, a button light guide member 63 configured to guide, towards the button 62, light emitted from the button circuit board 61, and a decorative button panel 64. The beauty instrument 100 may further include a charging interface 81, and the charging interface 81 is disposed at a tail of the beauty instrument 100. The beauty instrument 100 may further include an energy storage component such as a rechargeable battery, and the energy storage component is connected to the charging interface 81, to supply power to the beauty instrument 100 after being charged.

In some embodiments, as shown in FIG. 3 and FIG. 4, there is a first gap 45 between the heat dissipation body 41 and the housing body 10B to accommodate a button assembly. The button assembly may include the button circuit board 61, the button 62, and the button light guide member 63. Therefore, the first gap 45 may be formed to accommodate the button assembly, so that the button assembly is properly disposed.

In some embodiments, as shown in FIG. 3 and FIG. 4, the button circuit board 61 of the button assembly is mounted on one side surface of the heat dissipation body 41. For example, the button circuit board 61 may be mounted on a side surface that is of the heat dissipation body 41 and that faces a front-side protection panel 12. Therefore, the heat dissipation body 41 can support the button circuit board 61.

In some embodiments, as shown in FIG. 3 and FIG. 4, the button circuit board 61 and the mounting protrusion part 42 are spaced apart in the length direction of the housing 10, and the main control circuit board 71 is at least partially opposite to the mounting protrusion part 42. The main control circuit board 71 is disposed at an upper position and the button circuit board 61 is disposed at a lower position, so that a thickness of a lower end of the housing can be reduced.

In some embodiments, as shown in FIG. 6 and FIG. 7, the mounting protrusion part 42 includes a mounting panel 421 having the mounting surface 420 and a connection part 44 connecting the heat dissipation body 41 and the mounting panel 421. The mounting panel 421 is inclined relative to the length direction A1.

Specifically, both the mounting panel 421 and the heat dissipation body 41 are disposed in a substantially rectangular panel shape, and the connection part 44 connects the mounting protrusion part 42 and the heat dissipation body 41, so that the mounting protrusion part 42 is inclined and oriented relative to the heat dissipation body 41. The disposed connection part 44 is further configured to transfer heat from the mounting protrusion part 42 to the heat dissipation body 41.

In some embodiments, as shown in FIG. 6 and FIG. 7, the connection part 44 may be of a triangular structure. A first edge 441 thereof is connected to the mounting panel 421, a second edge 442 thereof is connected to the heat dissipation body 41, and a third edge 443 thereof and the mounting surface 420 of the mounting protrusion part 42 form an included angle in a range of 85 degrees to 95 degrees, for example, may be 85 degrees, 88 degrees, 90 degrees, 93 degrees, or 95 degrees.

It is noted herein that the triangular structure herein is with respect to a side view shape of the connection part 44, the first edge 441, the second edge 442, and the third edge 443 actually all correspond to surfaces of the connection part 44, but these surfaces are shown as lines in the side view. In this manner, structural design can be facilitated, and the connection part 44 can have proper structural strength, to support the mounting protrusion part 42.

In some embodiments, as shown in FIG. 6 and FIG. 8, the heat dissipation member 40 includes a hollow part 43, and the hollow part 43 communicates the connection pan 44 with the heat dissipation body 41. Therefore, the hollow part 43 may be formed to accommodate another component of the beauty instrument 100. In addition, the hollow part 43 may be further disposed to increase a heat dissipation area and reduce a quantity of used materials.

In some embodiments, as shown in FIG. 6 and FIG. 8, the hollow part 43 includes a first hollow part 431 and a second hollow part 432. The two hollow parts 43 are disposed, so that the connection part 44 can have uniform support strength.

Figure 10:
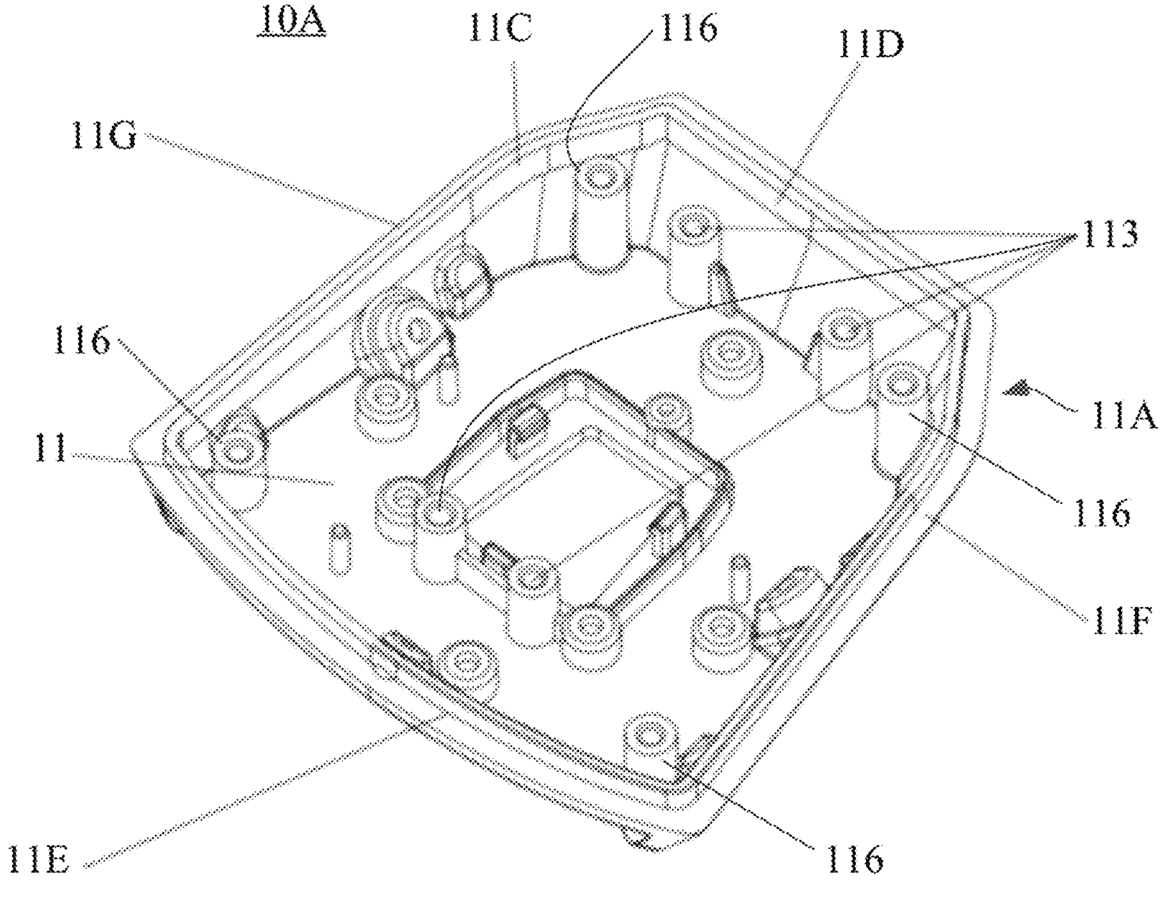
FIG. 10 is a schematic three-dimensional diagram of a working head of a beauty instrument according to some embodiments of this application.
Figure 25:
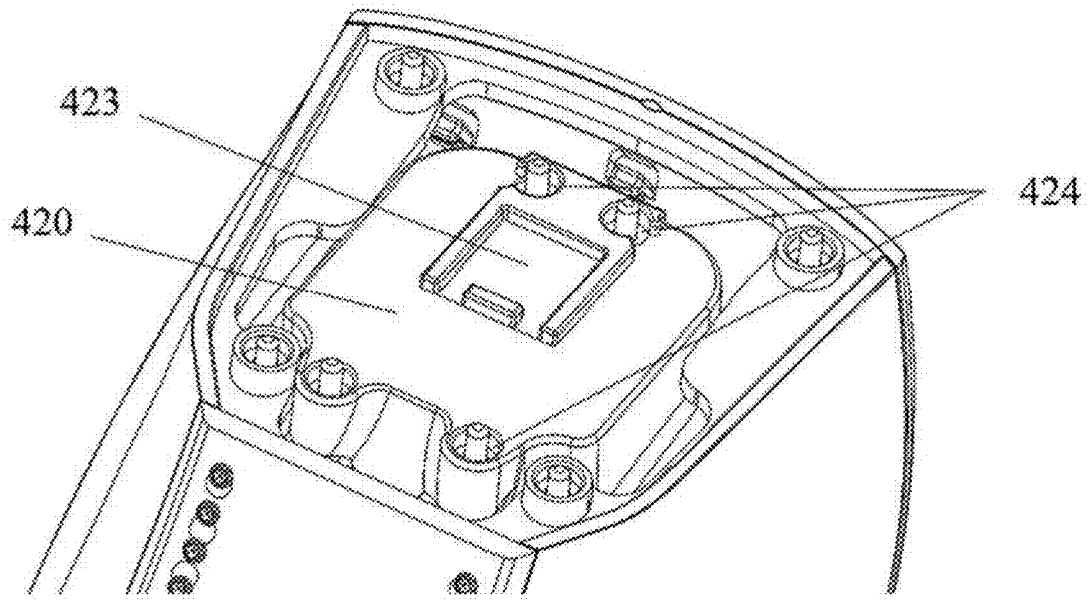
FIG. 25 is a schematic diagram of a partial structure of a beauty instrument according to some embodiments of this application.
Figure 26:
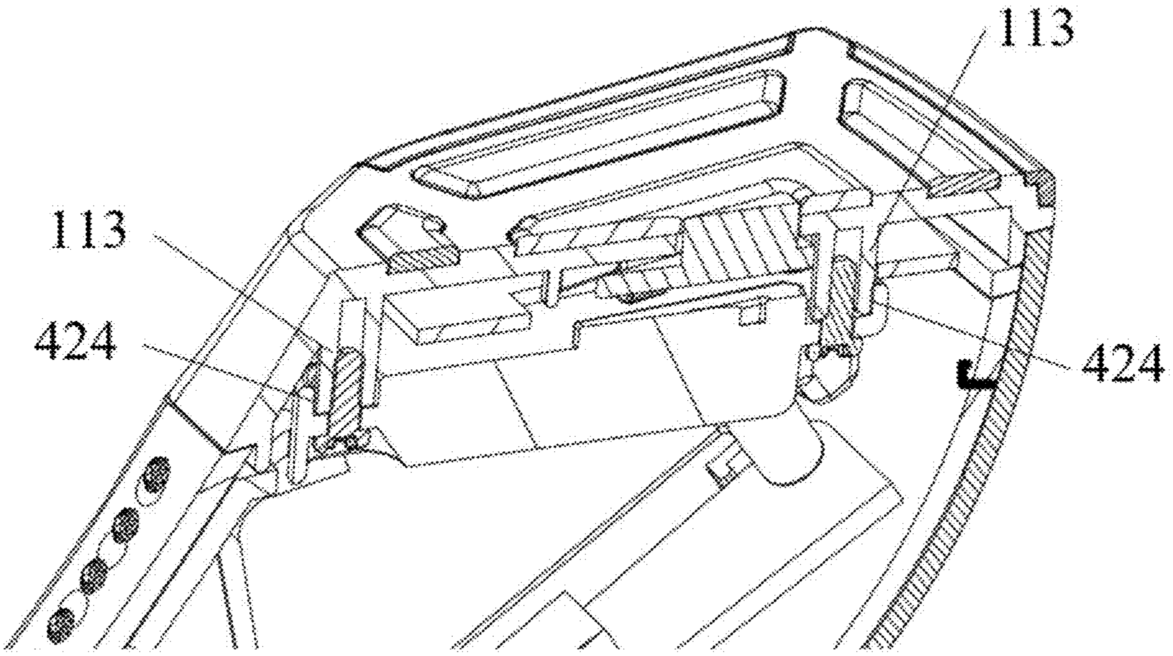
FIG. 26 is a schematic sectional view of a partial structure of a beauty instrument according to some embodiments of this application.

In some embodiments, as shown in FIG. 6, FIG. 10, and FIG. 25, FIG. 10 is a schematic three-dimensional diagram of a working head 10A of a beauty instrument according to some embodiments of this application, and FIG. 25 is a schematic diagram of a partial structure of a beauty instrument according to some embodiments of this application. A second fastener such as a screw may pass through the mounting protrusion part 42 to be detachably connected to the working head 10A.

For example, a fastening pillar 113 is convexly disposed on the working head 10A, and a connection hole 424 is disposed on the mounting panel 421. The second fastener such as a screw may pass through the connection hole 424 to be connected to the fastening pillar 113, so that the working head 10A is connected to the mounting protrusion part 42. There may be a hole inside the fastening pillar 113 for a screw to be screwed into the hole. The hole may be a threaded hole.

In some embodiments, as shown in FIG. 4, an end that is of the heat dissipation body 41 and that is away from the mounting protrusion part 42 is close to a rear side panel of the housing 10. For example, the end that is of the heat dissipation body 41 and that is away from the mounting protrusion part 42 may be in contact with an inner housing back cover 13 of the housing 10. Through such disposition, the heat dissipation body 41 can transfer heat to the inner housing back cover 13 of the housing 10, and then transfer the heat to a back cover 17 of the housing 10, to dissipate heat to the outside of the beauty instrument 100.

In some embodiments, with reference to FIG. 4, an end that is of the heat dissipation body 41 and that is away from the mounting protrusion part 42 is connected to a front side panel of the housing 10. The end that is of the heat dissipation body 41 and that is away from the mounting protrusion part 42 may be connected to the front-side protection panel 12 of the housing 10 by using a fastener such as a screw. For example, a mounting pillar 123 that protrudes towards the rear side panel is disposed on an inner side surface of the front side panel of the housing 10, and the end that is of the heat dissipation body 41 and that is away from the mounting protrusion part 42 is mounted on the mounting pillar 123, so that the end that is of the heat dissipation body 41 and that is away from the mounting protrusion part 42 is close to the rear side panel of the housing 10, and the end that is of the heat dissipation body 41 and that is away from the mounting protrusion part 42 is connected to the front side panel of the housing 10 by using a fastener. A through hole 411 may be disposed at the end that is of the heat dissipation body 41 and that is away from the mounting protrusion part 42, and a screw may be screwed into the mounting pillar 123 through the through hole 411, to implement connection between the heat dissipation body 41 and the front-side protection panel 12. In this manner, the thickness of the lower end (or referred to as the tail) of the housing 10 may be further reduced.

In some embodiments, with reference to FIG. 3 and FIG. 6, the second fastener passes through the mounting protrusion part 42 to be detachably connected to the working head 10A, so as to connect the mounting protrusion part 42 and the working head 10A. For example, the second fastener may be a screw, and the second fastener passes through the mounting protrusion part 42 and is screwed into the working head 10A, so that connection and mounting between the mounting protrusion part 42 and the working head 10A can be implemented. The detachable connection between the working head 10A and the mounting protrusion part 42 facilitates structural design, component assembly, and maintenance.

In some embodiments, with reference to FIG. 3, FIG. 6, FIG. 8, FIG. 10, and FIG. 26, FIG. 26 is a schematic sectional view of a partial structure of a beauty instrument according to some embodiments of this application. A plurality of connection holes 424 are disposed on the mounting protrusion part 42. The plurality of connection holes 424 are distributed around the barrier wall 422 to allow the second fastener to pass through. Corresponding fastening pillars 113 may be disposed on the working head 10A. Therefore, the second fastener passes through the connection hole 424 and is screwed into the corresponding fastening pillar 113 of the working head 10A, so that connection and mounting between the mounting protrusion part 42 and the working head 10A can be implemented. There may be at least three connection holes 424, so that the connection between the working head 10A and the mounting protrusion part 42 is stable. In the illustrated embodiment, there are four connection holes 424 that are distributed on two opposite sides of the mounting protrusion part 42, and two of the connection holes 424 may be disposed near two corners of the barrier wall 422. In this manner, reliable connection between the working head 10A and the mounting protrusion part 42 can be implemented. In addition, a fastening fastener penetrates from an inner side of the opening 10C, so that a connection structure can be hidden, and aesthetics and airtightness can be improved.

In some embodiments, as shown in FIG. 3, FIG. 4, and FIG. 7, the main control circuit board 71 of the beauty instrument 100 is disposed in the housing 10, the main control circuit board 71 extends in the length direction A1 of the housing 10, and the main control circuit board 71 is mounted on the heat dissipation body 41. The extension direction of the heat dissipation body 41 and an extension direction of the main control circuit board 71 may be parallel. In some embodiments, the main control circuit board 71 is located on the second side of the heat dissipation body 41. The main control circuit board 71 is disposed on the second side of the heat dissipation body 41, so that components in the beauty instrument 100 can be properly laid out, and the main control circuit board 71 can be supported by using the heat dissipation member 40.

In some embodiments, the main control circuit board 71 is spaced apart from the heat dissipation body 41. In this manner, heat transfer between the main control circuit board 71 and the heat dissipation body 41 can be avoided or reduced.

In some embodiments, as shown in FIG. 4 and FIG. 8, a support pillar 410 is disposed on the heat dissipation body 41, and the main control circuit board 71 is supported by the support pillar 410, and is spaced apart from the heat dissipation body 41. Through such disposition, heat of the heat dissipation body 41 can be prevented from being transferred to the main control circuit board 71.

In some embodiments, as shown in FIG. 2 to FIG. 4, the beauty instrument 100 may further include a handle 20. The housing 10 may include a working surface 110 and a rear side surface 170, and the rear side surface 170 is a surface that is not parallel to the working surface 110 to form a specific angle. The handle 20 may include a connection pillar 21 and a blocking part 22. A first end 211 of the connection pillar 21 is connected to the housing 10. The first end 211 of the connection pillar 21 may be mounted on the rear side surface 170, for example, connected to the back cover 17 of the housing 10, so that the connection pillar 21 extends away from the rear side surface 170. The blocking part 22 is connected to a second end 212 of the connection pillar 21, and limiting space 23 for insertion of a finger of the user is formed between the blocking part 22 and the rear side surface 170 of the housing 10. It is noted herein that the connection pillar 21 and the blocking part 22 may be an integral structure. There may be no structural boundary between the second end 212 and the blocking part 22. In other words, the second end 212 may be defined as any part that is of the connection pillar 21 and that is close to the blocking part 22.

In the beauty instrument 100 in the foregoing embodiment, the handle 20 is disposed on the housing 10, so that the user conveniently holds the beauty instrument 100, to easily move the beauty instrument 100 through push and pull, and perform various treatment such as beauty treatment and skin care on the skin of the user by moving the working surface 110 on the skin of the user. Specifically, when using the beauty instrument 100, the user may first insert two adjacent fingers into the limiting space 23, enable the two fingers to grip the connection pillar 21, and enable the other fingers to hold the housing 10, so that the palm is limited between the blocking part 22 and the housing 10. In this way, the beauty instrument 100 such as a beauty instrument can move on the face or another skin part by using the palm, to implement skin treatment such as beauty treatment.

It is easy to understand that the housing 10 of the beauty instrument 100 may be generally held by the user, and the handle 20 added in this application may add a holding manner. Therefore, the user may alternately use the beauty instrument 100 in this application in a plurality of manners, to avoid fatigue caused by a single manner.

In some embodiments, as shown in FIG. 2 and FIG. 4, the handle 20 is mounted at an upper position in the middle of the rear side surface 170. Therefore, in this application, a manner of using the handle 20 may allow a hand action position of the user to be closer to the skin, so that the working surface 110 is more evenly applied to the skin such as the face.

In some embodiments, as shown in FIG. 2 and FIG. 4, a first function button 24 is disposed on a side surface that is of the blocking part 22 and that is away from the housing 10. The first function button 24 may be an on/off button. Correspondingly, the first function button 24 may be disposed on the blocking part 22 to facilitate operation by the user.

In some embodiments, as shown in FIG. 2 and FIG. 4, the connection pillar 21 may be of a hollow structure, and the inside thereof is used to dispose a wire electrically connected to the first function button 24. The disposed wire may be connected to the first function button 24, passes through the hollow structure of the connection pillar 21, and then is connected to a circuit board inside the beauty instrument 100, so that a switch of the beauty instrument 100 can be controlled by using the first function button 24. Correspondingly, the connection pillar 21 may be disposed as a hollow structure to effectively use structural space of the handle 20.

Figure 12:
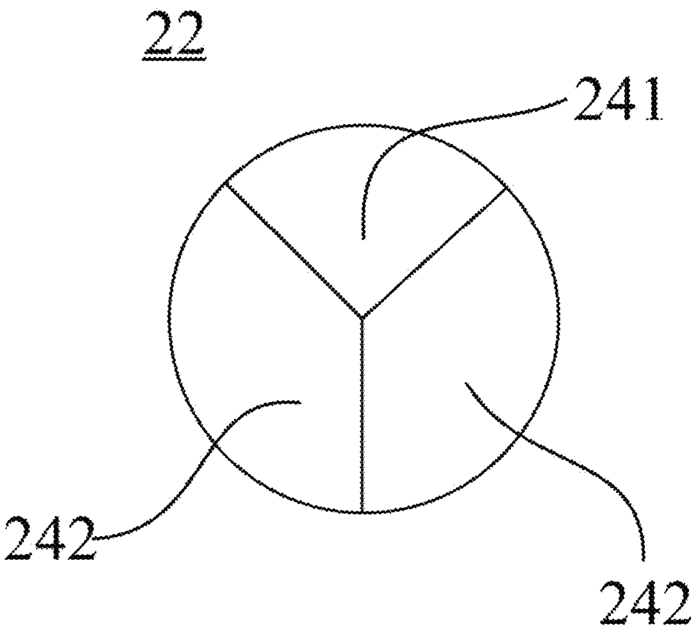
FIG. 12 is a schematic layout diagram of a first function button on a handle of a beauty instrument according to some embodiments of this application.

In some embodiments, as shown in FIG. 12, the first function button 24 may include an on/off button 241 and a function selection button 242 that are adjacent to each other. In other words, when structural space on the blocking part 22 is sufficient, in addition to the on/off button 241, one or more function selection buttons 242 may be disposed. Shapes of the on/off button 241 and the function selection button 242 may be designed based on a shape of the blocking part 22. In the embodiment shown in FIG. 12, one on/off button 241 and two function selection buttons 242 are disposed.

For example, the first function button 24 may include at least one of a touchscreen and a mechanical button. In other words, when one on/off button 241 is used, the on/off button 241 may be configured as a touchscreen or a mechanical button. When a plurality of function selection buttons 242 are used, each function selection button 242 may be configured as a touchscreen or a mechanical button. For another example, when a plurality of function selection buttons 242 are disposed, one function selection button 242 may be a button that enables the beauty instrument 100 to operate in a cleaning mode, and one function selection button 242 may be a button that enables the beauty instrument 100 to operate in a lifting mode. Correspondingly, the touchscreen may improve operation convenience, and the mechanical button may improve an operation sense during operation. In addition, a plurality of function buttons are integrated on an end face of the blocking part 22, thereby facilitating operation by the user.

In some embodiments, as shown in FIG. 2, a second function button 26 may be disposed on the rear side surface 170, and the second function button 26 is located on a side that is of the handle 20 and that is close to the working surface 110. In other words, the second function button 26 is located between the handle 20 and the working surface 110. Similarly, there may be one or more second function buttons 26, and the second function button 26 may include at least one of a touchscreen and a mechanical button. Correspondingly, these second function buttons 26 may be disposed as mouse-like buttons. Therefore, after the fingers grip the handle 20, different functions of the beauty instrument 100 can be controlled while the beauty instrument 100 is moved around the face/body skin, so that the beauty instrument 100 is controlled to work, and operation convenience is improved.

Figure 13:
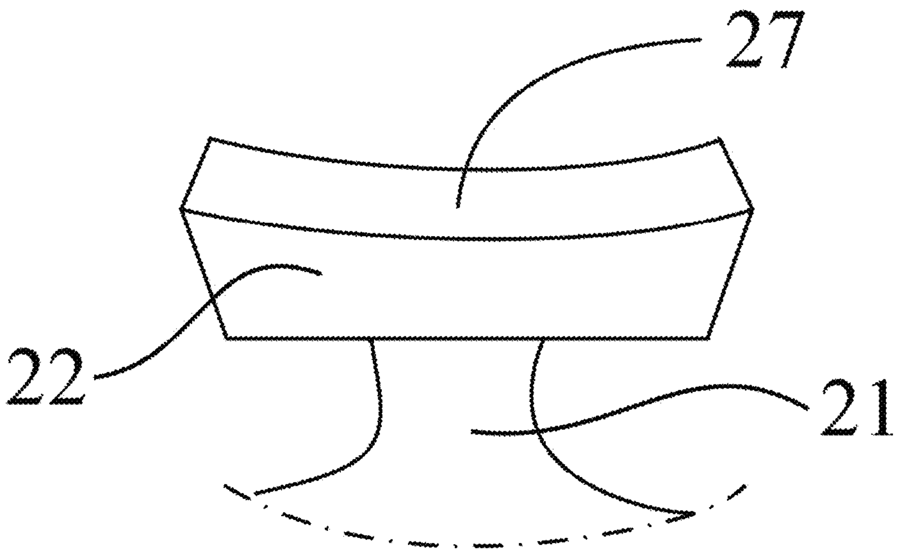
FIG. 13 is a schematic three-dimensional diagram of a handle of a beauty instrument according to some embodiments of this application.

In some embodiments, as shown in FIG. 2, the blocking part 22 is cylindrical. In other words, the blocking part 22 may be in a cylindrical shape with a short length, and a projection thereof on the rear side surface 170 is circular or substantially circular. Alternatively, FIG. 13 is a schematic three-dimensional diagram of a handle of a beauty instrument according to some embodiments of this application. In this embodiment, the blocking part 22 is in a porcelain pillow shape. In other words, a surface 27 that is of the blocking part 22 and that is away from the connection pillar 21 may be disposed as an arc-shaped surface. In addition, a surface that is of the blocking part 22 and that faces the connection pillar 21 may also be disposed as an arc-shaped surface. It is easy to understand that the cylindrical blocking part 22 is convenient for structural design and manufacture, and the porcelain pillow-shaped blocking part 22 is suitable for grip by the fingers of the user.

In some embodiments, with reference to FIG. 2 and FIG. 4, the connection pillar 21 is detachably connected to the housing 10. For example, the first end 211 of the connection pillar 21 may be inserted into the housing 10 to implement the detachable connection. Alternatively, the first end 211 of the connection pillar 21 is detachably mounted on the housing 10 by using a snap-fit structure. Alternatively, the first end 211 of the connection pillar 21 may be fastened to the housing 10 by using a structure such as a threaded pillar, or the first end 211 of the connection pillar 21 may be mounted on the housing 10 by using a screw. In these detachable connection manners, the handle 20 can be removed for easy storage when the beauty instrument 100 is not used.

Figure 20:
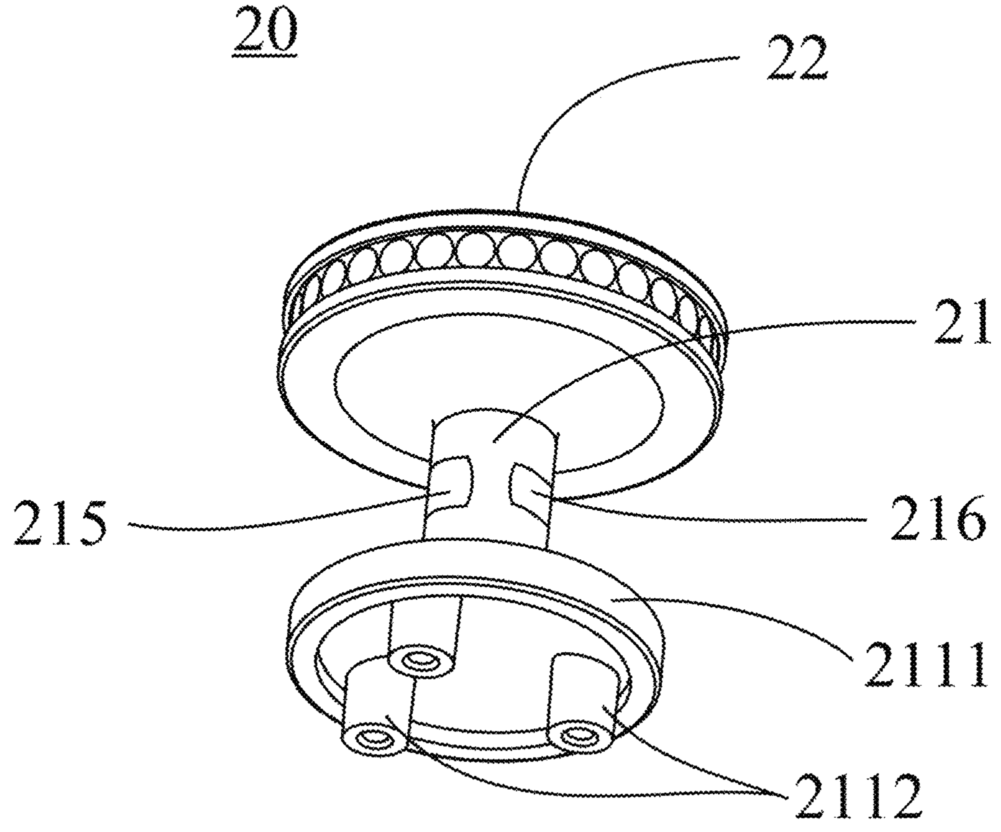
FIG. 20 is a schematic three-dimensional diagram of a handle of a beauty instrument according to some embodiments of this application.

In some embodiments, with reference to FIG. 2 to FIG. 4, the housing 10 includes a back cover 17 having a rear side surface 170, and the back cover 17 includes a recessed part 174 disposed on the rear side surface 170. With reference to FIG. 20, a connection component 2111 is disposed at the first end 211 of the connection pillar 21, and the connection component 2111 is mounted in the recessed part 174. Optionally, the connection component 2111 is disposed in a flattened shape as a whole, for example, is substantially in a panel shape.

Further, the housing 10 further includes an inner housing back cover 13, and the inner housing back cover 13 is disposed on an inner side of the back cover 17. The inner housing back cover 13 defines a mounting hole 134, and the recessed part 174 is inserted into the mounting hole 134. Specifically, a connection protrusion pillar 2112 is disposed on a side surface that is of the connection component 2111 and that is away from the connection pillar 21, a connection hole 175 is disposed at the bottom of the recessed part 174, the connection component 2111 is adaptively mounted in the recessed part 174, and the connection protrusion pillar 2112 is inserted into the connection hole 175. For example, a fastener such as a screw may pass through the connection hole 175 and be screwed into a threaded hole on the connection protrusion pillar 2112, thereby mounting the connection pillar 21 on the back cover 17.

The recessed part 174 is disposed to cooperate with the connection component 2111, so that a contact area between the connection pillar 21 and the back cover 17 can be increased, thereby increasing connection strength. In addition, a surface that is of the connection component 2111 and that faces the blocking part 22 may further smoothly transition with the rear side surface 170, thereby increasing comfort during use. The mounting hole 134 may form avoidance space for the recessed part 174 in a spatial structure, and the back cover 17 may be further limited through cooperation between the recessed part 174 and the mounting hole 134.

In some embodiments, as shown in FIG. 4, a reinforcement rib 214 may be disposed in the connection pillar 21. The reinforcement rib 214 may extend in a length direction of the connection pillar 21, and protrude into the hollow structure of the connection pillar 21. The reinforcement rib 214 may use a same material as the connection pillar 21, and be formed integrally with the connection pillar 21. Alternatively, the reinforcement rib may be a metal piece, and may be embedded and formed in the connection pillar 21. There may be one or more reinforcement ribs 214, and a cross-sectional shape thereof may be rectangular, partially circular, or the like, provided that a structure can be strengthened. The plurality of reinforcement ribs 214 may be evenly distributed in a circumferential direction of an interior hollow of the connection pillar 21. The reinforcement rib 214 is disposed, so that structural strength of the connection pillar 21 can be increased, thereby preventing damage caused by force during use.

In some embodiments, with reference to FIG. 1 to FIG. 4, the housing 10 includes a front cover 16 and a back cover 17, and the back cover 17 includes a rear side surface 170. The housing 10 is configured to: when the beauty instrument 100 works, enable the front cover 16 to be closer to to-be-treated skin of the user than the back cover 17. As shown in FIG. 2, at least at a position close to the working surface 110, a width of the back cover 17 in the width direction A2 perpendicular to the length direction A1 is greater than a width of the front cover 16. For example, near a position at which the handle 20 is disposed, the width of the back cover 17 may be greater than the width of the front cover 16. In this embodiment, the width of the back cover 17 on which the handle 20 is mounted is set to be greater than the width of the front cover 16, so that an area of the back cover 17 can be increased, thereby helping the palm of the user be in contact with and hold the back cover 17.

In some embodiments, with reference to FIG. 2 and FIG. 4, the rear side surface 170 includes a curved surface part 171 that protrudes backward, and the connection pillar 21 is disposed at the curved surface part 171. The curved surface part 171 may include an arc-shaped surface or a spherical surface. Therefore, the curved surface part 171 that protrudes backward can be disposed to match a palm surface of the palm of the user, thereby improving comfort during operation.

In some embodiments, with reference to FIG. 2 and FIG. 4, the connection pillar 21 is disposed at an end that is of the rear side surface 170 and that is close to the working surface 110. In other words, a disposition position of the connection pillar 21 on the rear side surface 170 is close to the working surface 110. In this manner, it is convenient for the user to apply force to a part of a skin treatment apparatus close to the working surface 110, so that the skin treatment apparatus can be operated with less effort.

In some embodiments, with reference to FIG. 3 and FIG. 4, the housing 10 includes a working head 10A having a top panel 11, and a front-side protection panel 12 and an inner housing back cover 13 that are opposite to each other. When the housing 10 is configured to: when the beauty instrument 100 works, enable the front-side protection panel 12 to be located on a side that is of the inner housing back cover 13 and that faces the human body. In other words, the front-side protection panel 12 is closer to to-be-treated skin of the user than the inner housing back cover 13. The top panel 11 may be in a flat panel shape, and the working surface 110 is formed on a side that is of the top panel 11 and that is away from a tail 101. The housing 10 further includes a left side panel 14 and a right side panel 15 that are opposite to each other and that are connected between the front-side protection panel 12 and the inner housing back cover 13. The left side panel 14 and the right side panel 15 may be perpendicular or inclined to the front-side protection panel 12. The front-side protection panel 12, the left side panel 14, and the right side panel 15 may be an integrally molded structure, and a whole thereof may be referred to as an inner housing skeleton, and may have an opening 10C. The inner housing skeleton, a connection panel 10F disposed in a ring shape, the front cover 16, the inner housing back cover 13, and the back cover 17 may constitute the housing body 10B.

The front-side protection panel 12, the inner housing back cover 13, the left side panel 14, and the right side panel 15 are disposed, to form a structural framework, so as to support the top panel 11. In addition, accommodation space surrounded by the side panels may be used to mount an internal component.

Correspondingly, the front cover 16 may be disposed on the front-side protection panel 12, and the back cover 17 may be disposed on the inner housing back cover 13.

When the beauty instrument 100 includes the back cover 17, the rear side surface 170 is located on the back cover 17. When the beauty instrument 100 does not include the back cover 17 but includes the inner housing back cover 13, the rear side surface 170 is located on the inner housing back cover 13.

The front-side protection panel 12, the left side panel 14, and the right side panel 15 are disposed as an integrally molded structure, to facilitate structural manufacture and mounting.

The inner housing skeleton can play a main role of structural support, and the back cover 17 and the front cover 16 can play an auxiliary role of structural support, and can also have a decorative effect.

In some embodiments, with reference to FIG. 3, the beauty instrument 100 may further include a left support panel 18 and a right support panel 19, and the left support panel 18 and the right support panel 19 are mounted in the housing 10, and are disposed between the left side panel 14 and the right side panel 15. The left support panel 18 and the right support panel 19 are disposed. Therefore, a component such as a circuit board may be disposed thereon, and structural strength of the housing may be increased.

In some embodiments, with reference to FIG. 3 to FIG. 5, the working head 10A is detachably connected to the housing body 10B by using a first fastener, and covers the opening 10C. The first fastener may be a screw that passes through the housing body 10B and is screwed into the working head 10A to implement connection and mounting between the housing body 10B and the working head 10A. The detachable connection between the working head 10A and the housing body 10B facilitates structural design, component assembly, and maintenance.

Figure 14:
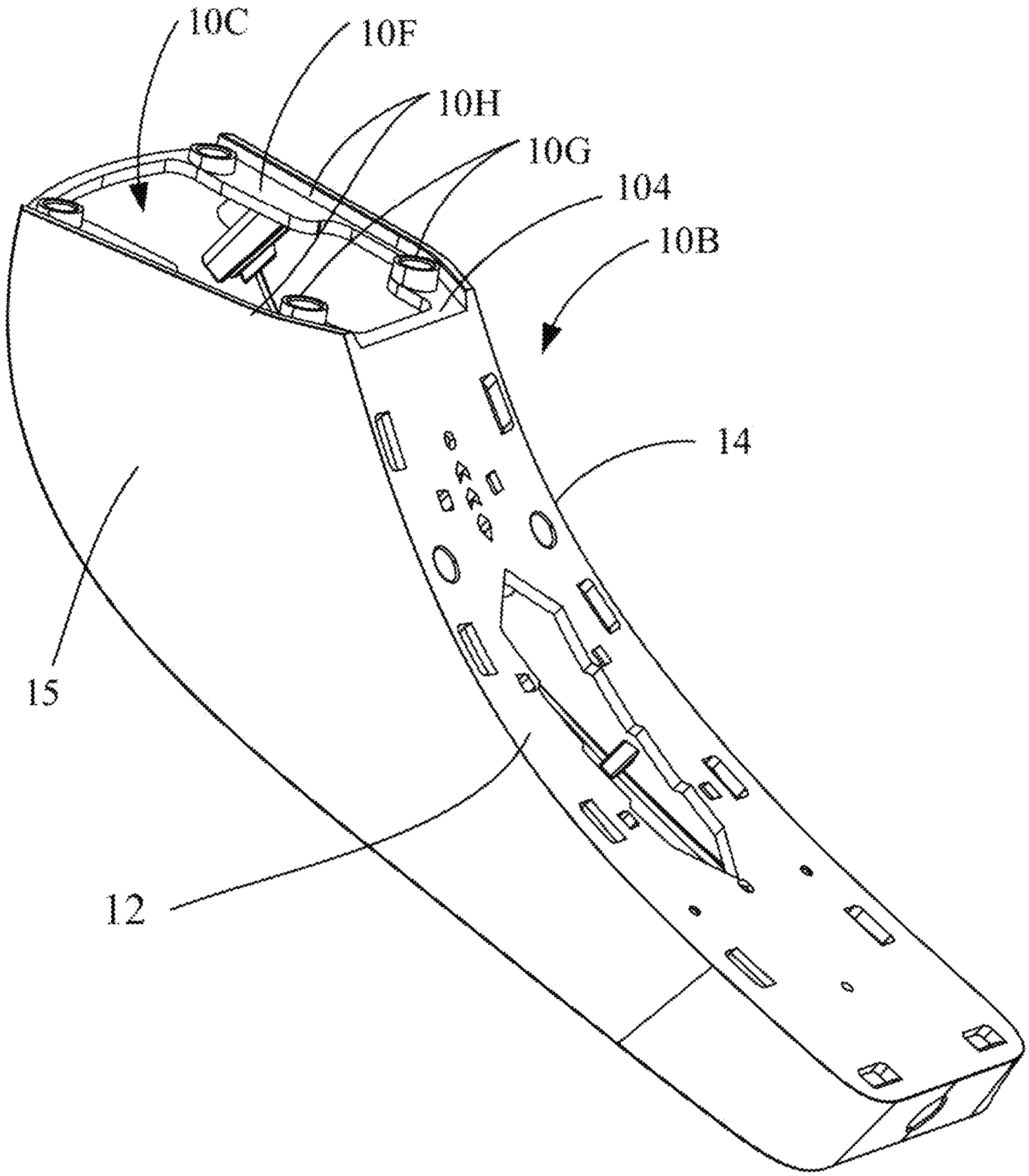
FIG. 14 is a schematic enlarged view of a partial structure of a housing body of a beauty instrument according to some embodiments of this application.

In some embodiments, with reference to FIG. 3 and FIG. 14, FIG. 14 is a schematic enlarged view of a partial structure of a housing body 10B of a beauty instrument according to some embodiments of this application. The housing body 10B includes a connection panel 10F having an opening 10C. A plurality of connection pillars 10G are disposed on the connection panel 10F. The plurality of connection pillars 10G are distributed around the opening 10C, to allow a first fastener such as a screw to pass through. The connection pillar 10G may be disposed as a hollow structure, and a corresponding connection pillar may be disposed on the working head 10A. Therefore, the first fastener passes through the connection pillar 10G, and is screwed into a corresponding connection pillar (namely, a fastening protrusion part 116) of the working head 10A, thereby implementing connection and mounting between the housing body 10B and the working head 10A. There may be at least three connection pillars 10G, so that the connection between the working head 10A and the housing body 10B is stable. In the illustrated embodiment, there are four connection pillars 10G, and the four connection pillars 10G are distributed near four corners of the opening 10C. In this manner, reliable connection between the working head 10A and the housing body 10B can be implemented. In addition, a fastening fastener penetrates from the bottom of the connection panel 10F, so that a connection structure can be hidden, and aesthetics and airtightness can be improved.

Figure 9:
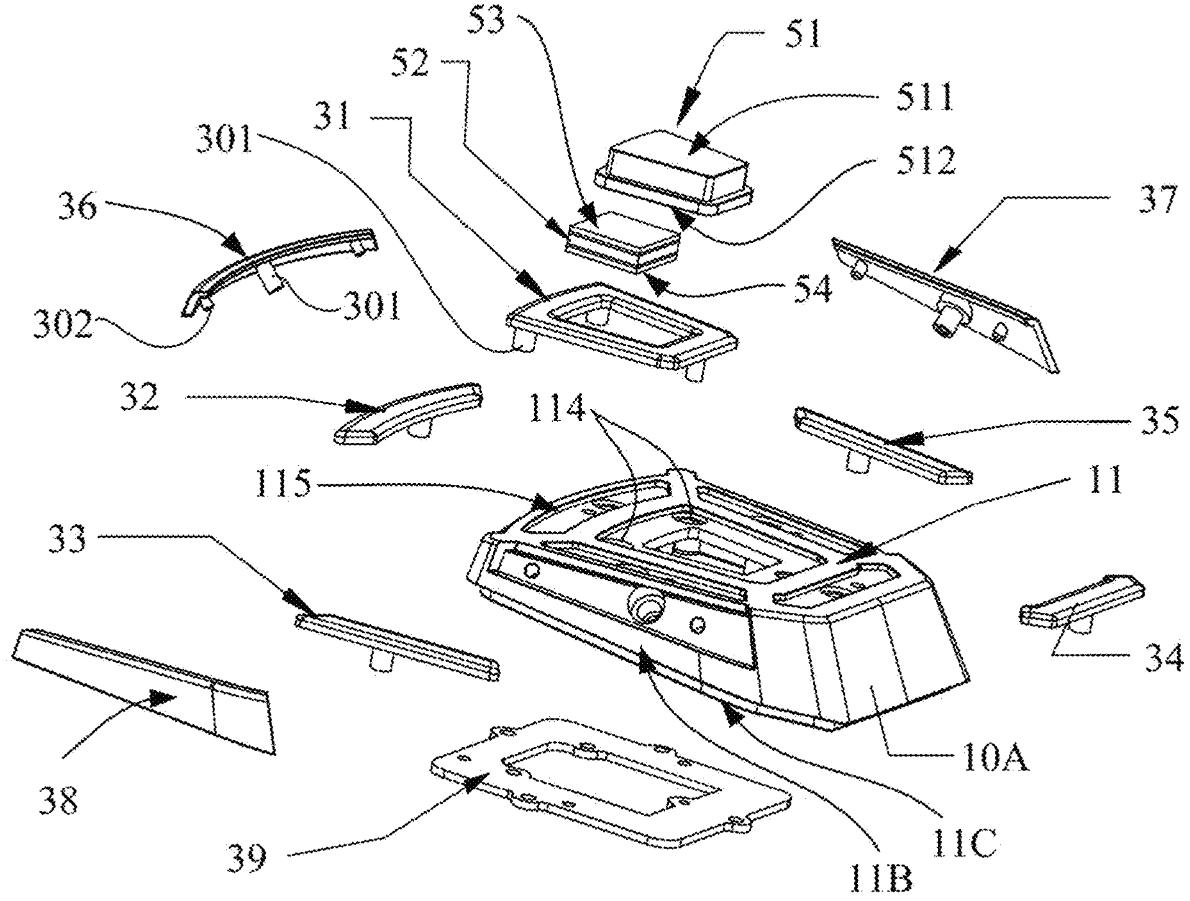
FIG. 9 is an enlarged exploded schematic diagram of a head assembly of a beauty instrument according to some embodiments of this application.

In some embodiments, with reference to FIG. 9 and FIG. 14, the housing body 10B includes a joining wall 10H that extends from the connection panel 10F to the working head 10A, and the joining wall 10H is in contact and cooperates with a side wall 11B of the working head 10A. It should be noted that, in the embodiment shown in FIG. 14, the joining wall 10H is formed on an upper end of the left side panel or the right side panel, and is configured to form a receiving slot 104. For example, a top surface of the joining wall 10H may abut on and be in contact with a lower surface of the side wall 11B, to implement contact and cooperation between the joining wall 10H and the side wall 11B. Further, the side wall 11B of the working head 10A may further extend downward on an inner side to form a limiting ring protrusion 11C. During assembly, an outer side surface of the limiting ring protrusion 11C may be in contact and cooperate with an inner side surface of the joining wall 10H. Because the limiting ring protrusion 11C is disposed, the joining wall 10H is disposed to extend from the connection panel 10F to the working head 10A by a specific height. The height may be equal to or slightly higher than a height of the limiting ring protrusion 11C, and the joining wall 10H may also have a same height as the connection pillar 10G. In this manner, the working head 10A may be more stably mounted on the housing body 10B.

In some embodiments, with reference to FIG. 1 to FIG. 4, the working surface 110 is inclined to the length direction A1. Because the working surface 110 is inclined to the length direction A1, the working surface 110 forms an inclined angle with both the front-side protection panel 12 and the inner housing back cover 13. Therefore, compared with a working surface 110 perpendicular to both the front-side protection panel 12 and the inner housing back cover 13, the working surface 110 in this application may have a large area, so that a large quantity of electrodes 30 can be disposed, or an area of a single electrode 30 can be large, thereby implementing a good beauty effect. In addition, it is easier to cooperate with a new holding manner of the handle, to improve comfort during use.

In some embodiments, the foregoing inclined angle may be optionally less than or equal to 45 degrees, for example, less than or equal to 30 degrees, and greater than or equal to 10 degrees, for example, optionally 12 degrees, 15 degrees, 18 degrees, 20 degrees, or 25 degrees. A proper inclined angle is selected, so that a large working surface can be provided, and the new holding manner conforms to a use habit of the user, to prevent the arm from lifting excessively high, and improve/ensure comfort during use.

In some embodiments, with reference to FIG. 1 to FIG. 4, the housing 10 includes atop panel 11, a front side panel and a rear side panel that are opposite to each other.

It should be noted that, in this application, the front side panel may be a single panel body, or may be a stacked panel assembly. For example, in the embodiment shown in FIG. 3, the front side panel includes the front-side protection panel 12 and the front cover 16, and the rear side panel includes the inner housing back cover 13 and the back cover 17. In some other embodiments, the front side panel in this application may include at least one of the front-side protection panel 12 and the front cover 16, and the rear side panel may include at least one of the inner housing back cover 13 and the back cover 17.

In the embodiment provided in this application, the front side panel includes the front-side protection panel 12, the rear side panel includes the inner housing back cover 13, the front-side protection panel 12 forms a main structure of the front side panel, and the inner housing back cover 13 forms a main structure of the rear side panel. Therefore, in some descriptions in this specification, the front-side protection panel 12 is sometimes used to represent the front side panel, and the inner housing back cover 13 is sometimes used to represent the rear side panel.

In some embodiments, with reference to FIG. 1 to FIG. 4, both the front side panel and the rear side panel are arc-shaped panels in the length direction A1, and a distance between the front side panel and the rear side panel at least partially increases gradually in a direction from the tail 101 of the housing to the head 102, so that an end that is of the heat dissipation body 41 and that is away from the mounting protrusion part 42 is close to the rear side panel of the housing 10, and the end that is of the heat dissipation body 41 and that is away from the mounting protrusion part 42 is connected to the front side panel of the housing 10.

The beauty instrument 100 is configured to: during working, enable the front-side protection panel 12 to face the skin of the user, the top panel 11 has the working surface 110, and the electrode 30 is mounted on the top panel 11 and exposed to the working surface 110. The housing 10 has the length direction A1, the top panel 11 is located at the head 102 of the housing, both the front side panel and the rear side panel are arc-shaped panels in the length direction A1, and the distance between the front side panel and the rear side panel at least partially increases gradually in the direction from the tail 101 of the housing to the head 102. An upper end of the inner housing back cover 13 protrudes from an upper end of the front-side protection panel 12 in the length direction A1, a front side edge 111 of the top panel 11 is supported at the upper end of the front-side protection panel 12, and a rear side edge 112 of the top panel 11 is supported at the upper end of the inner housing back cover 13, so that the working surface 110 is inclined to the length direction A1.

In the thickness direction A3 perpendicular to the length direction A1, a distance is formed between the front-side protection panel 12 and the inner housing back cover 13. The front side edge 111 of the top panel 11 may be directly or indirectly supported at the upper end of the front-side protection panel 12, and the rear side edge 112 of the top panel 11 may be directly or indirectly supported at the upper end of the inner housing back cover 13. In the illustrated embodiment, the front side edge 111 of the top panel 11 is indirectly supported at the upper end of the front-side protection panel 12, and the rear side edge 112 of the top panel 11 is indirectly supported at the upper end of the inner housing back cover 13. In other words, the front side edge 111 of the top panel 11 is supported at the upper end of the front-side protection panel 12 by using an annular side panel 11A connected to the top panel, and the rear side edge 112 of the top panel 11 is supported at the upper end of the inner housing back cover 13 by using the annular side panel 11A. The annular side panel 11A extends from a periphery of the top panel 11 to a same side of the top panel 11, to surround accommodation space with the top panel 11.

In the beauty instrument 100 in the foregoing embodiment, because the distance between the front-side protection panel 12 and the inner housing back cover 13 at least partially increases gradually from the tail 101 to the head 102, a distance between the upper end of the front side panel and the upper end of the rear side panel is greater than a distance between a lower end of the front side panel and a lower end of the rear side panel, and the upper end of the rear side panel protrudes from the upper end of the front side panel in the length direction A1, so that the working surface 110 is inclined to the length direction A1. In this way, the working surface 110 may have a large area, so that a large quantity of electrodes 30 can be disposed, or an area of a single electrode 30 can be large, to implement a good beauty effect. In addition, the lower end that is of the housing 10 and that is close to the tail 101 is convenient for holding.

In the beauty instrument 100 in the foregoing embodiment, the working surface 110 forms an inclined angle with both the front-side protection panel 12 and the inner housing back cover 13

Figure 15:
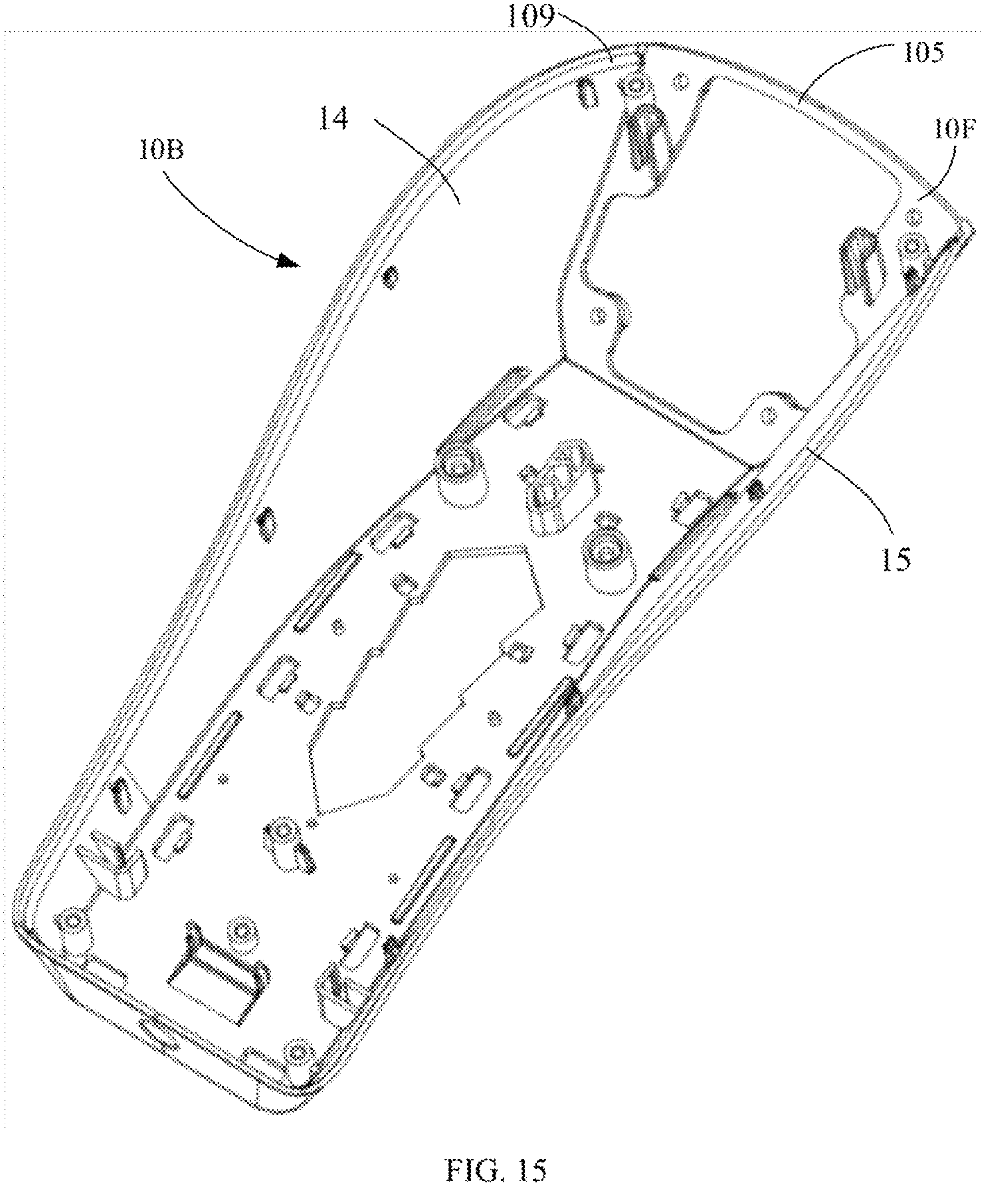
FIG. 15 is another schematic three-dimensional diagram of a partial structure of a housing body of a beauty instrument according to some embodiments of this application.

In some embodiments, with reference to FIG. 14 and FIG. 15, FIG. 15 is another schematic three-dimensional diagram of a partial structure of a housing body 10B of a beauty instrument according to some embodiments of this application. A receiving slot 104 is formed at a periphery of the opening 10C of the housing body 10B. With reference to FIG. 9 and FIG. 10 again, the working head 10A includes a top panel 11 and an annular side panel 11A connected to a periphery of the top panel 11. The electrode 30 is mounted on the top panel 11 and/or the annular side panel 11A (for example, an upper edge electrode 36, a left edge electrode 37, and a right edge electrode 38 are mounted on a connection part between the top panel 11 and the annular side panel 11A), the top panel 11 and/or the annular side panel 11A are/is connected to the mounting protrusion part 42, and a lower end of the annular side panel 11A abuts on the receiving slot 104.

In this manner, the working head 10A may be more stably mounted on the housing body 10B.

It should be noted that, in this application, the working head 10A is mounted at the opening of the housing body in the foregoing manner, the heat dissipation member 40 is connected to the working head 10A, and the heat dissipation member 40 is fixedly mounted in the housing body 10B. In this way, the working head 10A may be fastened by using the heat dissipation member 40, and the heat dissipation member 40 may be fastened by using the working head 10A, so that the heat dissipation member 40, the working head 10A, and the housing body 10B interact with each other, to form a simple and stable mounting structure.

In some embodiments, with reference to FIG. 14 and FIG. 15, the housing body 10B may include a front-side protection panel 12, a connection panel 10F disposed in a ring shape, and a left side panel 14 and a right side panel 15 that are connected to two sides of the front-side protection panel 12. The connection panel 10F is located between the left side panel 14 and the right side panel 15, and an outer periphery of the connection panel 10F is connected to the front-side protection panel 12, the left side panel 14, and the right side panel 15. Upper side edges of both the left side panel 14 and the right side panel 15 protrude from the connection panel 10F to form the receiving slot 104 between the connection panel 10F and both the left side panel 14 and the right side panel 15.

In this way, the receiving slot 104 is formed by using a skeleton structure (the front-side protection panel 12, the left side panel 14, and the right side panel 15) of the housing body and the connection panel 10F, so that a structure of the receiving slot 104 is simple. In addition, the receiving slot 104 is formed, so that the working head 10A can be more stably mounted on the housing body 10B.

In some embodiments, with reference to FIG. 14 and FIG. 15, the front-side protection panel 12, the left side panel 14, and the right side panel 15 are integrally connected to the connection panel 10F. In this way, the component may be manufactured in an integral injection molding manner. In this manner, structural design and manufacture are facilitated.

In some embodiments, with reference to FIG. 3, FIG. 14, and FIG. 15, an upper side edge of the front-side protection panel 12 is connected to the connection panel 10F, the housing body 10B further includes a front cover 16, the front cover 16 is disposed on a front side surface of the front-side protection panel 12, and an upper side edge of the front cover 16 protrudes from the connection panel 10F, to form the receiving slot 104. In this way, a lower end of the annular side panel 11A may be hidden by using the front cover 16.

In some embodiments, with reference to FIG. 3, FIG. 14, FIG. 15, and FIG. 16, FIG. 16 is a partial schematic three-dimensional diagram of a housing body of a beauty instrument according to some embodiments of this application, where a structure of a connection panel 10F is mainly shown. The housing 10 further includes a rear side panel, the rear side panel is opposite to the front-side protection panel 12, and an upper side edge of the rear side panel protrudes from the connection panel 10F, to form the receiving slot 104. The connection panel 10F includes a rear panel 105 opposite to the front-side protection panel 12, and an accommodation slot 109 is formed between the rear panel 105, a rear side edge of the left side panel 14, and a rear side edge of the right side panel 15.

In some embodiments, with reference to FIG. 3, FIG. 14, and FIG. 15, the rear side panel includes an inner housing back cover 13 and a back cover 17 disposed on a rear side of the inner housing back cover 13. The inner housing back cover 13 is mounted in the accommodation slot 109, and an upper side edge of the back cover 17 protrudes from the connection panel 10F, to form the receiving slot 104.

In this way, the accommodation slot 109 is formed by using the connection panel, to mount the inner housing back cover 13. In addition, a lower end of the annular side panel 11A may be hidden by using the upper side edge of the back cover 17.

Figure 16:
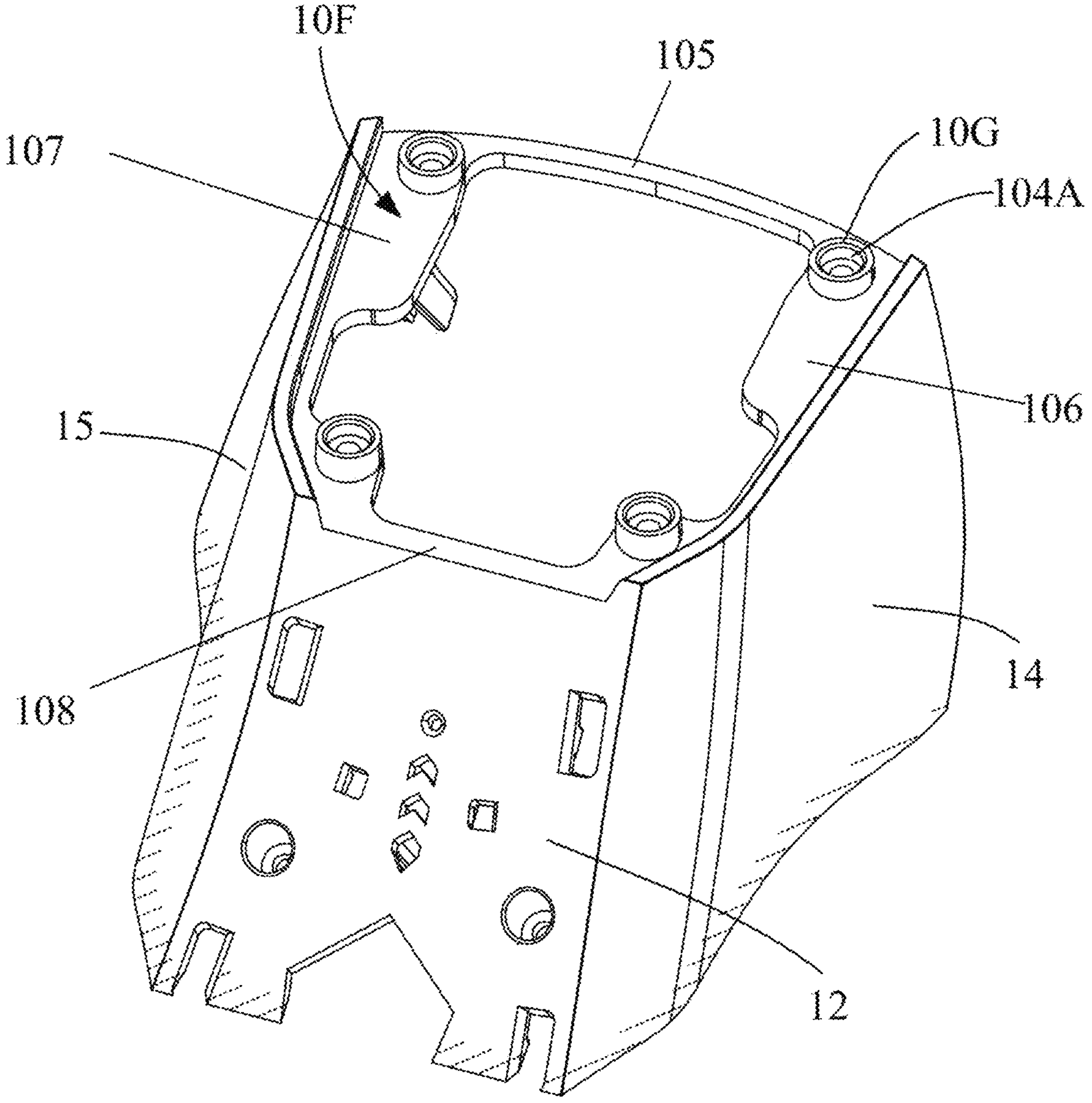
FIG. 16 is a partial schematic three-dimensional diagram of a housing body of a beauty instrument according to some embodiments of this application, where a structure of a connection panel is mainly shown.

In some embodiments, with reference to FIG. 14, FIG. 15, and FIG. 16, the connection panel 10F includes a left panel 106 disposed on an inner side of the left side panel 14, a right panel 107 disposed on an inner side of the right side panel 15, and a front panel 108 connected to the front-side protection panel 12. A connection part between the left panel 106 and the front panel 108 may be connected to the top panel 11. A connection part between the right panel 107 and the front panel 108 may be connected to the top panel 11.

For example, with reference to FIG. 10, a fastener (for example, a first fastener such as a screw) may pass through the connection part between the left panel 106 and the front panel 108 to be connected to the fastening protrusion part 116 of the top panel 11, and a fastener may pass through the connection part between the right panel 107 and the front panel 108 to be connected to the fastening protrusion part 116 of the top panel 11. Specifically, a connection pillar 10G is formed at the connection part between the left panel 106 and the front panel 108, the connection pillar 10G is correspondingly provided with a fastening protrusion part 116, and a fastener may pass through the connection pillar 10G to be connected to the fastening protrusion part 116 corresponding to the connection pillar 10G.

For example, a connection pillar 10G is formed at the connection part between the right panel 107 and the front panel 108, the connection pillar 10G is correspondingly provided with a fastening protrusion part 116, and a fastener may pass through the connection pillar 10G to be connected to the fastening protrusion part 116 corresponding to the connection pillar 10G.

In some embodiments, with reference to FIG. 9 and FIG. 10, the annular side panel 11A includes a front enclosure panel 11D and a rear enclosure panel 11E that are opposite to each other, and an included angle between the front enclosure panel 11D and the top panel 11 is greater than 90 degrees, for example, may be 92 degrees, 95 degrees, 100 degrees, or 110 degrees.

In this way, the front enclosure panel 11D may smoothly transition with the front side panel.

Optionally, a protrusion height of the front enclosure panel 11D is greater than a protrusion height of the rear enclosure panel 11E.

In this way, a connection structure between the head cover and the housing body can be conveniently disposed.

In some embodiments, with reference to FIG. 9 and FIG. 10, the annular side panel 11A includes a left enclosure panel 11F and a right enclosure panel 11G that are opposite to each other, and an included angle between the left enclosure panel 11F and the top panel 11 is greater than 90 degrees, for example, may be 92 degrees, 95 degrees, 100 degrees, or 110 degrees. An included angle between the right enclosure panel 11G and the top panel 11 is greater than 90 degrees, for example, may be 92 degrees, 95 degrees, 100 degrees, or 110 degrees.

In this way, the included angle between the top panel 11 and each of the front enclosure panel 11D, the left enclosure panel 11F, and the right enclosure panel 11G is greater than 90 degrees, so that the working surface can be attached to the skin.

In some embodiments, a protrusion height of the left enclosure panel 11F gradually decreases from the front to the back.

In some embodiments, a protrusion height of the right enclosure panel 11G gradually decreases from the front to the back.

In some embodiments, with reference to FIG. 9, FIG. 10, FIG. 11, and FIG. 14, FIG. 11 is a schematic sectional view of a beauty instrument according to some embodiments of this application. A limiting ring protrusion 11C is convexly disposed on an end face of a lower end of the annular side panel 11A, and the limiting ring protrusion 11C abuts on the receiving slot 104.

In some embodiments, with reference to FIG. 4, FIG. 14, and FIG. 16, the top panel 11 is connected to the connection panel 10F. For example, a connection pillar 10G with a connection through hole 104A is disposed on the connection panel 10F, and the top panel 11 is connected to the connection panel 10F by using the connection through hole 104A.

Figure 11:
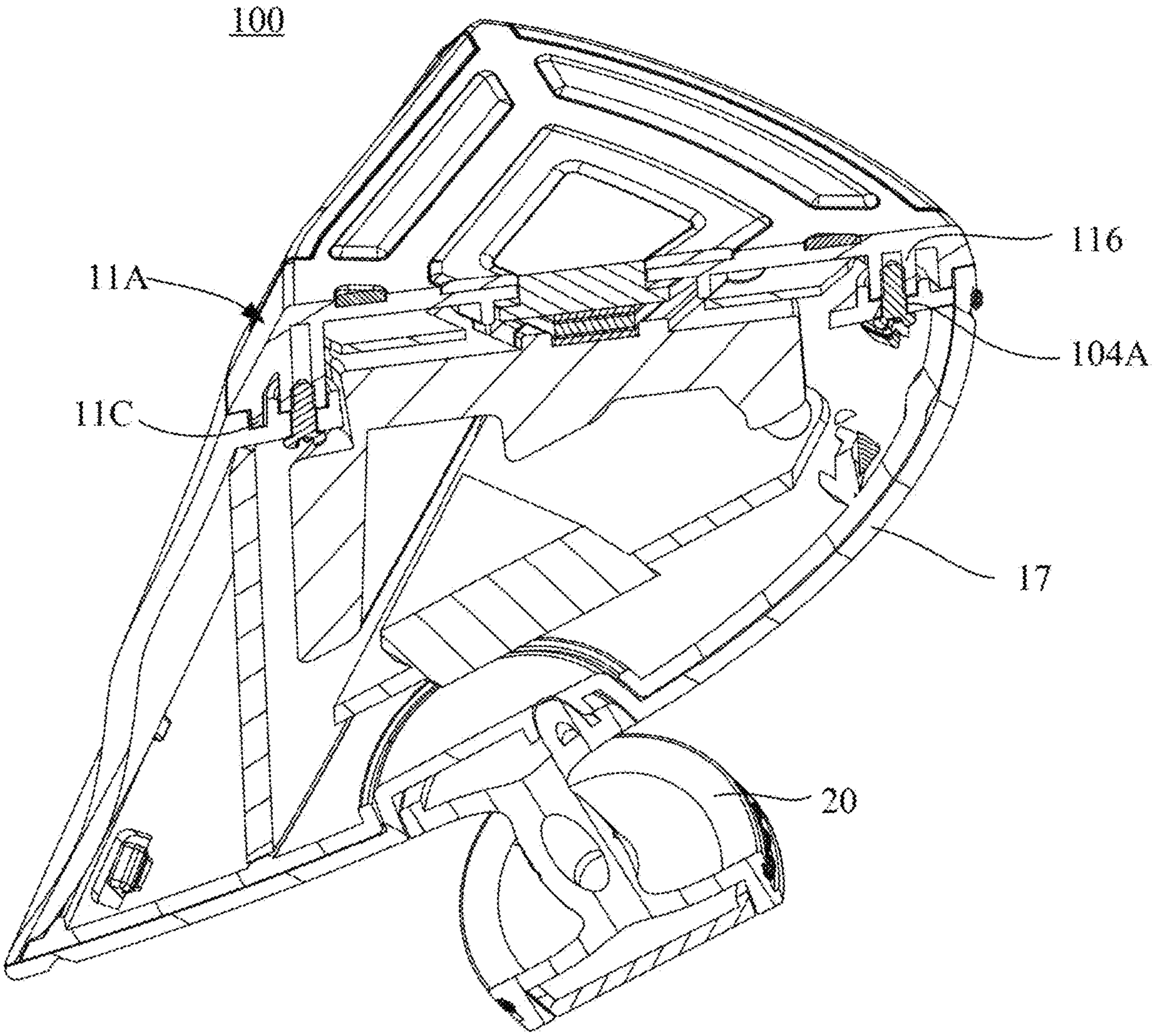
FIG. 11 is a schematic sectional view of a beauty instrument according to some embodiments of this application.

In some embodiments, with reference to FIG. 9, FIG. 10, FIG. 11, FIC. 14, and FIG. 16, a receiving slot 104 is formed at a periphery of the opening 10C of the housing body 10B, the working head 10A includes a top panel 11 and an annular side panel 1A connected to a periphery of the top panel 11, and the electrode 30 is mounted on the top panel 11 and/or the annular side panel 11A. A fastening protrusion part 116 is convexly disposed on an inner side surface of the working head 10A, the fastening protrusion part 116 is connected to the bottom of the receiving slot 104, and a lower end of the annular side panel 11A abuts on the receiving slot 104.

In this application, the receiving slot is formed at the opening 10C of the housing body, and the fastening protrusion part is disposed on the inner side surface of the working head 10A to be connected to the bottom of the receiving slot, so that the working head and the housing body can be limited in a direction in which the working head and the housing body are away from each other. In addition, the lower end of the annular side panel abuts on the receiving slot, so that the working head and the housing body can be limited in a direction in which the working head and the housing body are close to each other.

In this way, the working head may be fixedly mounted at the opening of the housing body. In addition, the receiving slot is formed at the opening of the housing body to cooperate with the fastening protrusion part on the working head, so that the fastening protrusion part can be disposed on the inner side surface of the working head. Therefore, design space of the fastening protrusion part can be increased, a size of the fastening protrusion part can be increased, and structural strength of the fastening protrusion part can be increased, to reduce a risk of damage during assembly or disassembly of the fastening protrusion part.

In addition, because design space of the fastening protrusion part may be increased, the fastening protrusion part may be designed as a fastening pillar with a threaded hole.

In some embodiments, a connection through hole 104A is disposed at the bottom of the receiving slot 104, and a fastener passes through the connection through hole 104A to be connected to the fastening protrusion part 116 in a threaded manner. A fastening fastener penetrates from the bottom of the receiving slot, so that the connection structure can be hidden, and aesthetics and airtightness can be improved.

In some embodiments, the fastening protrusion part 116 may be a fastening pillar. In some other embodiments, the fastening protrusion part 116 is an elastic snap, and a snap-joint that cooperates with the elastic snap is formed at the bottom of the receiving slot 104.

In some embodiments, the top panel 11 is inclined relative to the length direction A1 of the housing.

In some embodiments, the fastening protrusion part 116 is disposed on an inner side surface of the top panel 11.

In some embodiments, with reference to FIG. 1, FIG. 2, and FIG. 4, an outer peripheral side surface of the annular side panel 11A is transitionally connected to an outer peripheral side surface of the housing body 10B. In this manner, a head surface of the beauty instrument can be smooth, thereby improving user comfort during use.

In some embodiments, with reference to FIG. 1, FIG. 2, FIG. 5, and FIG. 9, a limiting ring protrusion 11C is convexly disposed on an end face of a lower end of the annular side panel 11A, and the limiting ring protrusion 11C adaptively abuts on the receiving slot 104. The side wall 11B of the working head 10A may extend downward on an inner side to form the limiting ring protrusion 11C. Because the limiting ring protrusion 11C is disposed, the working head 10A may be more stably mounted on the housing body 10B.

Figure 28:
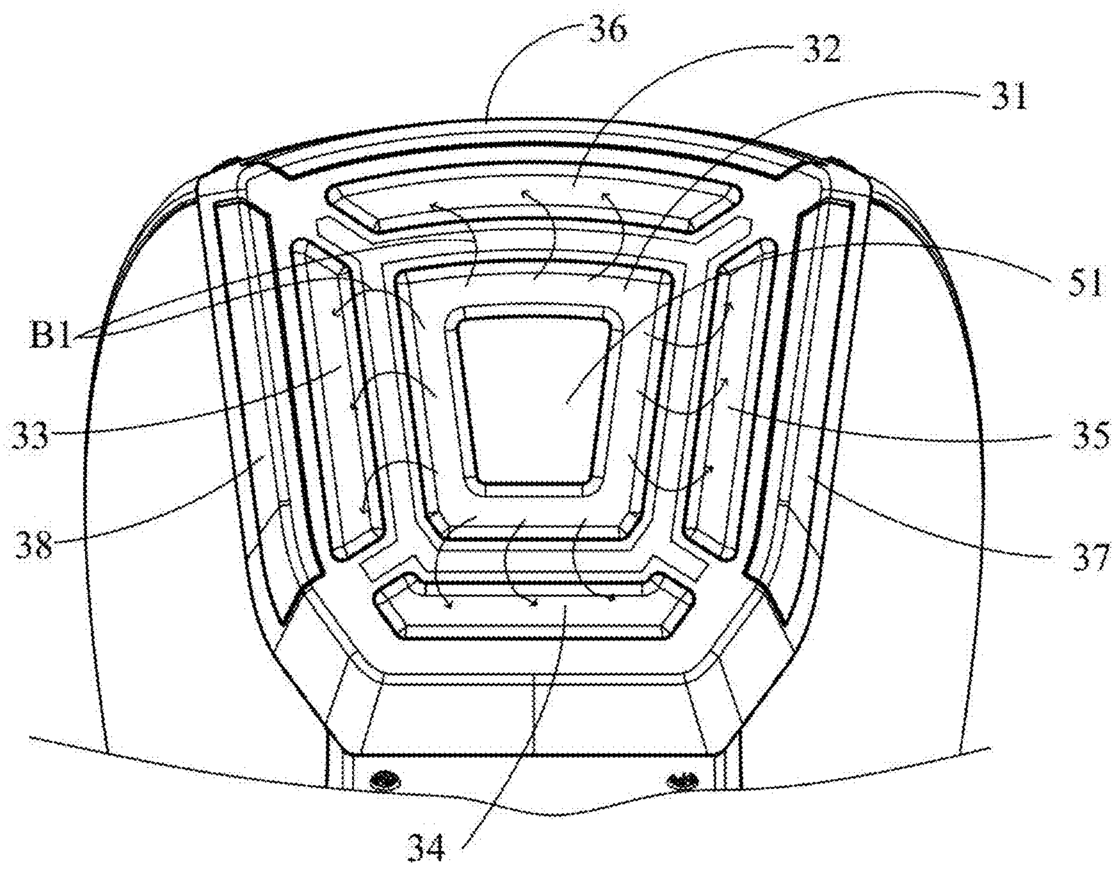
FIG. 28 is a schematic diagram of a working manner of an electrode of a beauty instrument according to some embodiments of this application.
Figure 29:
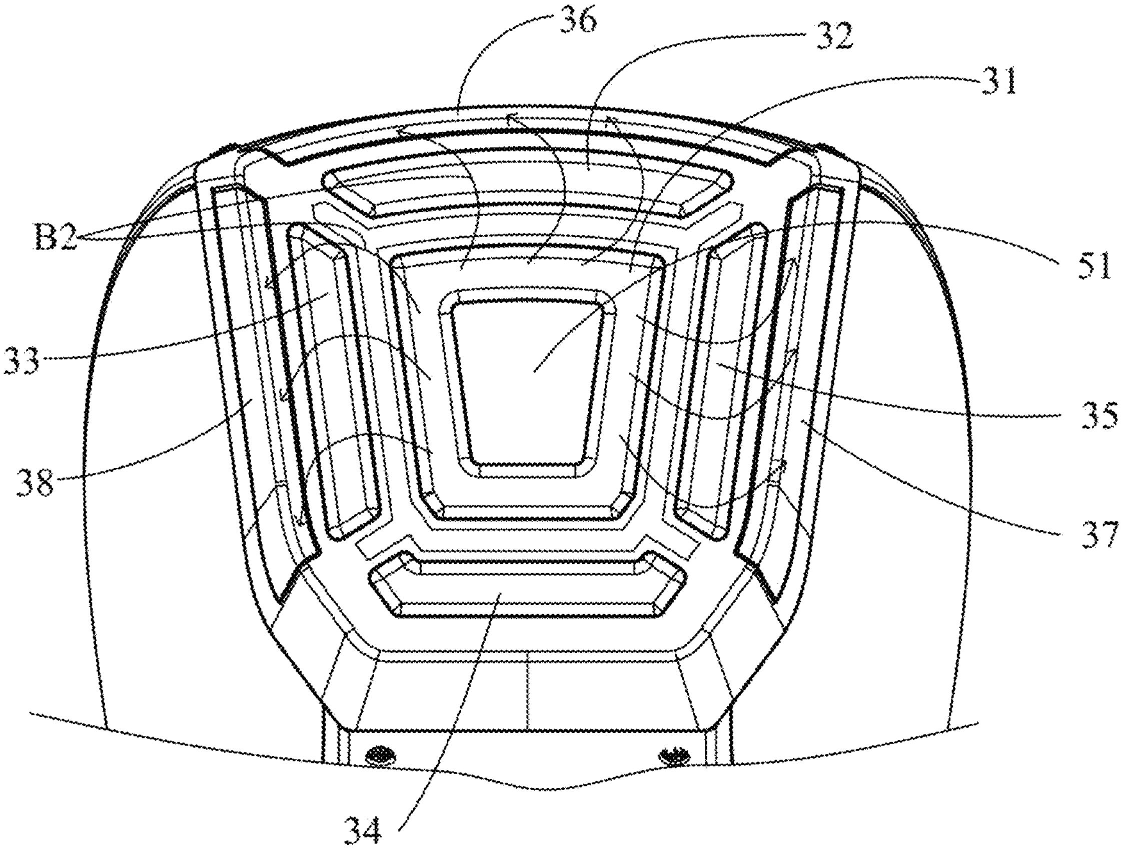
FIG. 29 is a schematic diagram of another working manner of an electrode of a beauty instrument according to some embodiments of this application.

In some embodiments, with reference to FIG. 1, FIG. 4, FIG. 9, FIG. 28, and FIG. 29, FIG. 28 is a schematic diagram of a working manner of an electrode of a beauty instrument according to some embodiments of this application, and FIG. 29 is a schematic diagram of another working manner of an electrode of a beauty instrument according to some embodiments of this application. The beauty instrument 100 may include: an electrical stimulation component, where the electrical stimulation component includes an EMS stimulation circuit 72, an RF radio frequency circuit 73, and a ring electrode, a first group of electrodes, and a second group of electrodes that are all disposed on the working head 10A, the ring electrode is separately connected to the EMS stimulation circuit 72 and the RF radio frequency circuit 73, the first group of electrodes includes a plurality of first electrodes, the plurality of first electrodes are all connected to the RF radio frequency circuit 73 and/or the EMS stimulation circuit (72), the plurality of first electrodes are distributed at intervals around the ring electrode, the second group of electrodes includes a plurality of second electrodes, the plurality of second electrodes are all connected to the EMS stimulation circuit (72), and the plurality of second electrodes are distributed at intervals around the first group of electrodes. The EMS stimulation circuit 72 and the RF radio frequency circuit 73 may be disposed on the main control circuit board 71.

The ring electrode and the first group of electrodes may form an RF radio frequency circuit to perform radio frequency beauty treatment on the skin. As shown in FIG. 28. RF may be sprayed from the inside to the outside in a first arrow direction B1, for example, from the ring electrode to the first group of electrodes through the skin. Alternatively. RF may be sprayed from the outside to the inside, to form a surging radio frequency energy field for beauty treatment.

It is understood that the radio frequency can penetrate the epidermis and reach the dermis, so that electromagnetic energy is converted into heat energy that can slightly and controllably burn the dermis to damage the collagen (slightly aged) existing in the dermis, thereby stimulating a repair mechanism of the skin, and producing new collagen to replace the collagen damaged by the heat energy.

The ring electrode and the second group of electrodes may form an EMS stimulation circuit to perform microcurrent beauty treatment on the skin. As shown in FIG. 29, EMS may be sprayed from the inside to the outside in a second arrow direction B2, for example, from the ring electrode first group of electrodes to the second group of electrodes through the skin. Alternatively, EMS may be sprayed from the outside to the inside.

It may be understood that EMS is a microcurrent, the microcurrent is a low-level current, and the face may be stimulated by sending a gentle electric wave to the facial muscle by using the skin and the tissues. The microcurrent may stimulate generation of ATP (or the microcurrent is used to stimulate muscle movement and accelerate synthesis of facial collagen), stimulate vitality of the facial muscle, and facilitate generation of the collagen and the elastin. In this way, the muscle and lymph are stimulated by using a weak current, to contract the muscle, so as to reduce edema and lift and tighten the skin.

In addition, in this application, the plurality of first electrodes are disposed around the ring electrode, so that a surging radio frequency energy field can be formed between the plurality of first electrodes and the ring electrode. The plurality of second electrodes are disposed around the first group of electrodes, so that a surging microcurrent energy field can be formed between the plurality of second electrodes and the ring electrode. In addition, when the EMS and the RF radio frequency are used alternately or simultaneously, because the ring electrode is shared, the microcurrent energy field may cover the radio frequency energy field, thereby implementing mutual enhancement.

The beauty instrument 100 in this application has a radio frequency function that may focus energy on the dermis to stimulate regeneration of the collagen and tighten the skin, and further has an EMS microcurrent stimulation function that stimulates the muscle and lymph by using a weak current, to contract the muscle, so as to reduce edema and lift and tighten the skin. When the beauty instrument is used with skin care products and targeted anti-aging essence, an EMS microcurrent can also open a surface channel of the skin to accelerate nutrient absorption.

It should be noted that when the plurality of first electrodes am all connected to the EMS stimulation circuit 72, a surging EMS energy field may be formed between the plurality of first electrodes and the ring electrode. An RF function is implemented by using another electrode.

In some embodiments, with reference to FIG. 1, FIG. 9, FIG. 27, FIG. 28, and FIG. 29, the ring electrode includes a ring electrode 31. It may be understood that the ring electrode is in the center, and a size thereof on the portable beauty instrument is generally small. Therefore, the ring electrode is disposed as an integrated ring electrode, so that the ring electrode can have a large size (compared with a case in which the ring electrode is divided into a plurality of small electrodes), and a current can be prevented from accumulating on the small electrode, to avoid a sting.

Specifically, the ring electrode may be a center electrode 31. In some other embodiments, the ring electrode may be a plurality of small electrodes distributed in a ring shape.

Figure 27:
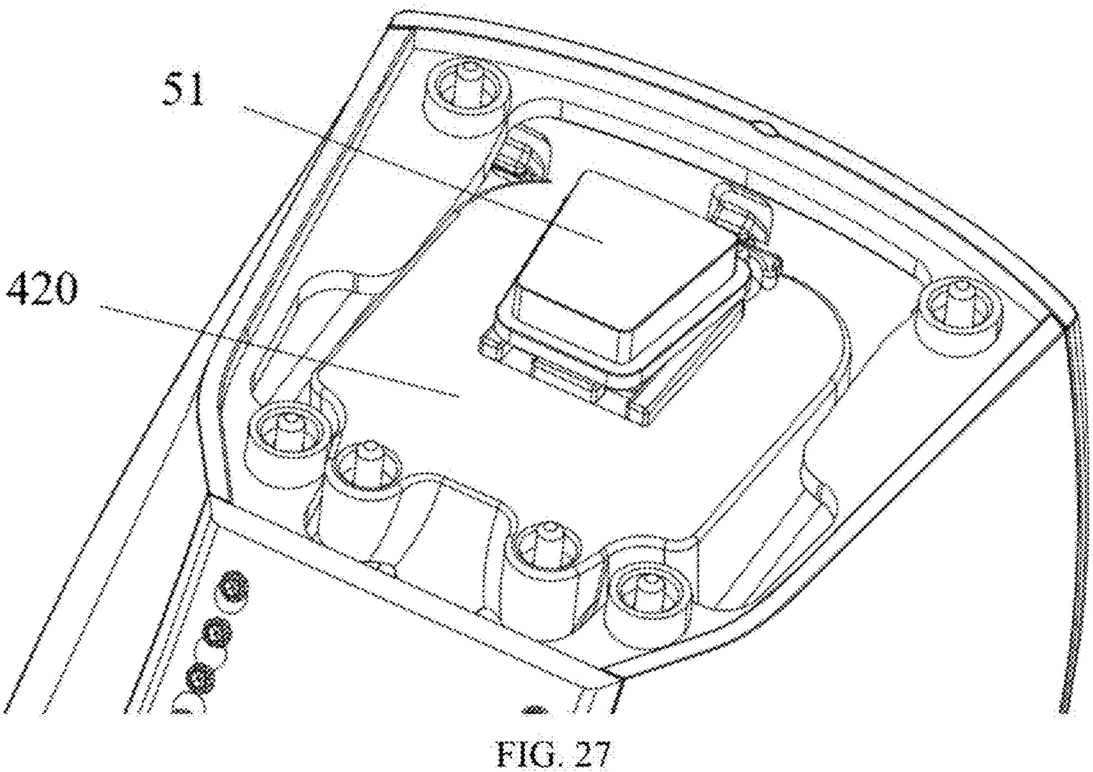
FIG. 27 is a schematic diagram of another partial structure of a beauty instrument according to some embodiments of this application.

In some embodiments, with reference to FIG. 1, FIG. 9, FIG. 27, FIG. 28, and FIG. 29. FIG. 27 is a schematic diagram of another partial structure of a beauty instrument according to some embodiments of this application. The beauty instrument 100 further includes a cold compress member 51, the cold compress member 51 includes a transparent crystal mounted on the working head 10A, and the ring electrode such as the center electrode 31 is disposed around the transparent crystal. Optionally, the center electrode 31 abuts on the transparent crystal.

In some embodiments, with reference to FIG. 1, FIG. 9, FIG. 27, FIG. 28, and FIG. 29, the ring electrode is in a polygonal ring shape, a quantity of first electrodes is the same as a quantity of edges of the ring electrode, and the plurality of first electrodes each correspond to one edge of the ring electrode. In this manner, each electrode edge of the ring electrode may cooperate with a corresponding first electrode to form an RF energy field, to facilitate energy allocation.

In some embodiments, with reference to FIG. 1, FIG. 9, FIG. 27, FIG. 28, and FIG. 29, the ring electrode is in a quadrilateral ring shape. There may be four first electrodes, and the four first electrodes each correspond to one edge of the ring electrode. The four first electrodes may be respectively an upper electrode 32, a right electrode 33, a lower electrode 34, and a left electrode 35. In this manner, each electrode edge of the ring electrode may cooperate with a corresponding first electrode to form an RF energy field, to facilitate energy allocation. In some other embodiments, the ring electrode may be in a ring shape.

For ease of explanation of this application, with reference to FIG. 25, there are three first electrodes: an upper electrode 32, a right electrode 33, and a left electrode 35. The three electrodes are all connected to the RF circuit, but a lower electrode 34 is not connected to the RF circuit. In this case, "the first group of electrodes includes a plurality of first electrodes, the plurality of first electrodes are all connected to the RF radio frequency circuit (73), and the plurality of first electrodes are distributed at intervals around the ring electrode", as mentioned in this application. In other words, "around" defined in this application includes "full around" and "half around".

In some embodiments, with reference to FIG. 1, FIG. 9, FIG. 27, FIG. 28, and FIG. 29, the ring electrode is in a quadrilateral ring shape, there may be three second electrodes, and the second third electrodes each correspond to one of three edges of the ring electrode. The three second electrodes may be respectively an upper edge electrode 36, a left edge electrode 37, and a right edge electrode 38.

In some embodiments, with reference to FIG. 1, FIG. 9, FIG. 27, FIG. 28, and FIG. 29, the ring electrode is in a quadrilateral ring shape, there are four first electrodes, the four first electrodes each correspond to one side of the ring electrode, and the four first electrodes are respectively an upper electrode 32, a right electrode 33, a lower electrode 34, and a left electrode 35; and there are three second electrodes, the three second electrodes each correspond to one of three edges of the ring electrode, the second electrodes are disposed at an edge of the working head 10A, and the three second electrodes are respectively an upper edge electrode 36, a left edge electrode 37, and a right edge electrode 38.

The upper edge electrode 36 may be an arc-shaped electrode.

In some embodiments, with reference to FIG. 1, FIG. 9, FIG. 27, FIG. 28, and FIG. 29, the working head 10A has the working surface 110 inclined to the length direction A1 of the housing 10, the ring electrode and the first group of electrodes are mounted on the working surface 110, and an upper-side width of the working surface 110 is greater than a lower-side width. The four first electrodes are respectively an upper electrode 32, a right electrode 33, a lower electrode 34, and a left electrode 35, and a length of the upper electrode 32 is greater than a length of the lower electrode 34. The upper electrode 32 may be an arc-shaped electrode.

It may be understood that the upper edge electrode 36 and the upper electrode 32 have large lengths, and are disposed in an arc shape, to facilitate energy aggregation.

In some embodiments, two ends of the lower electrode are provided with parts bent upward.

In some embodiments, the ring electrode includes an upper electrode edge and a lower electrode edge, and a length of the upper electrode edge is greater than a length of the lower electrode edge.

In some embodiments, the ring electrode may be disposed in a trapezoid shape or substantially in a trapezoid shape.

In some embodiments, at least a part of the plurality of first electrodes are connected to the EMS stimulation circuit 72.

In some embodiments, with reference to FIG. 1, FIG. 9, FIG. 27, FIG. 28, and FIG. 29, there are four first electrodes, and the four first electrodes are respectively an upper electrode 32, a right electrode 33, a lower electrode 34, and a left electrode 35; there are three second electrodes, the three second electrodes are respectively an upper edge electrode 36, a left edge electrode 37, and a right edge electrode 38, the upper electrode 32 corresponds to the upper edge electrode 36, the right electrode 33 corresponds to the right edge electrode 38, and the left electrode 35 corresponds to the left edge electrode 37; and at least one of the upper electrode 32, the right electrode 33, and the left electrode 35 is connected to the EMS stimulation circuit 72. For example, the upper electrode 32 and the upper edge electrode 36 may cooperate to form an EMS circuit, to remove nasolabial folds; and/or the right electrode 33 and the right edge electrode 38 may cooperate to form an EMS circuit, to remove nasolabial folds.

In some embodiments, with reference to FIG. 9, FIG. 28, and FIG. 29, the ring electrode includes an upper electrode edge, a left electrode edge, a right electrode edge, and a lower electrode edge, the four first electrodes are respectively an upper electrode 32, a right electrode 33, a lower electrode 34, and a left electrode 35, there are three second electrodes, the second electrodes are disposed at an edge of the working head 10A, and the three second electrodes are respectively an upper edge electrode 36, a left edge electrode 37, and a right edge electrode 38.

The upper electrode edge corresponds to the upper electrode 32 and the upper edge electrode 36, the left electrode edge corresponds to the left electrode 35 and the left edge electrode 37, the right electrode edge corresponds to the right electrode 33 and the right edge electrode 38, and the lower electrode edge corresponds to the lower electrode 34.

In some embodiments, with reference to FIG. 9, FIG. 28, and FIG. 29, a distance between the upper electrode edge and the upper electrode 32 is greater than a distance between the upper electrode 32 and the upper edge electrode 36, and/or a distance between the left electrode edge and the left electrode 35 is greater than a distance between the left electrode 35 and the left edge electrode 37; and/or a distance between the right electrode edge and the right electrode 33 is greater than a distance between the right electrode 33 and the right edge electrode 38.

It may be understood that RF energy is large, so that a distance between RF electrode pairs (such as the upper electrode edge and the upper electrode 32, the left electrode edge and the left electrode 35, and the right electrode edge and the right electrode 33) can be large, to cover a large beauty area. EMS energy is small, so that a distance between EMS electrode pairs such as the upper electrode 32 and the upper edge electrode 36 can be small, to perform EMS beauty treatment on a specific part such as a part with nasolabial folds.

In some embodiments, the ring electrode is in a polygonal ring shape, and at least a part of the plurality of first electrodes are in a one-to-one correspondence with edges of the ring electrode. In other words, when a quantity of first electrodes is greater than a quantity of edges of the ring electrode, only a part of first electrodes need to be in a one-to-one correspondence with the edges of the ring electrode.

The ring electrode is in a polygonal ring shape, and the plurality of first electrodes are in a one-to-one correspondence with at least a part of edges of the ring electrode. In other words, when a quantity of first electrodes is less than a quantity of edges of the ring electrode, only at least a part of the edges of the ring electrode need to be in a one-to-one correspondence with the plurality of first electrodes.

In some embodiments, with reference to FIG. 4 and FIG. 9, the ring electrode, the second first group of electrodes, and the second group of electrodes are mounted on the working head 10A by using a fastener. The ring electrode is used as an example for description herein. The ring electrode is the center electrode 31, and the center electrode 31 is mounted on the working head 10A by using a fastener such as a screw. The fastener may pass through the working head 10A from an inner side of the working head 10A and be screwed into the center electrode 31, to fasten the working head 10A and the center electrode 31.

In some embodiments, with reference to FIG. 4, FIG. 5, and FIG. 9, at least one of the ring electrode, the first group of electrodes, and the second group of electrodes has a connection protrusion part 301, the working head 10A is provided with a connection groove 114, and the connection protrusion part 301 is inserted into the connection groove 114, and the connection protrusion part 301 is fastened in the connection groove 114 by using the fastener. The ring electrode is used as an example for description herein. The ring electrode is the center electrode 31, and a connection protrusion part 301 is disposed on a side that is of the center electrode 31 and that faces the working head 10A. The connection protrusion part 301 may be in a protrusion pillar shape, and the connection groove 114 may be a groove formed in a protrusion pillar structure of the working head 10A. In this manner, the connection protrusion part 301 is inserted into the connection groove 114, and a fastener such as a screw passes through the working head 10A from an inner side of the working head 10A and is screwed into the center electrode 31, to fasten the working head 10A and the center electrode 31. The connection groove 114 is formed in the protrusion pillar structure, so that a good guiding and positioning function can be performed on the connection protrusion part 301.

In some embodiments, with reference to FIG. 4 and FIG. 9, at least one of the ring electrode, the first group of electrodes, and the second group of electrodes has a positioning protrusion pillar 302, and the positioning protrusion pillar 302 is inserted into the working head 10A. The upper edge electrode 36 in the second group of electrodes is used as an example for description herein. The upper edge electrode 36 has a positioning protrusion pillar 302, and a positioning hole that matches the positioning protrusion pillar 302 is disposed on the working head 10A. In this manner, the positioning protrusion pillar 302 is inserted into the positioning hole of the working head 10A, so that the upper edge electrode 36 is positioned through insertion and cooperation between the positioning protrusion pillar 302 and the positioning hole, to prevent the upper edge electrode 36 from moving relative to the working head 10A. A structure of the positioning protrusion pillar 302 is applicable to a case in which a length of the electrode is large, so that the positioning protrusion pillar can be mainly disposed on the second group of electrodes. The positioning protrusion pillar may be used or not used for the ring electrode and the first group of electrodes based on a situation.

In some embodiments, with reference to FIG. 4 and FIG. 9, the working head 10A is provided with an accommodation groove 115, and at least one of the ring electrode, the first group of electrodes, and the second group of electrodes is accommodated by the accommodation groove 115. The upper electrode 32 in the first group of electrodes is used as an example for description herein. The working head 10A is provided with an accommodation groove 115 that is structurally complementary to the bottom of the upper electrode 32, so that the upper electrode 32 can be accommodated by using the accommodation groove 115, to play an auxiliary role of positioning the upper electrode 32.

In some embodiments, with reference to FIG. 4 and FIG. 9, the electrode circuit board 39 of the beauty instrument 100 is disposed on a side that is of the working head 10A and that faces away from the ring electrode, the first group of electrodes, and the second group of electrodes, and at least one of the ring electrode, the first group of electrodes, and the second group of electrodes is fixedly connected to the electrode circuit board 39 by using the fastener. The electrode circuit board 39 may be configured to fasten the electrode and perform transfer for the electrode. The lower electrode 34 in the first group of electrodes is used as an example for description herein. The electrode circuit board 39 is disposed on an inner side of the working head 10A, and a fastener such as a screw successively passes through the electrode circuit board 39 and the working head 10A from the inner side of the working head 10A, and is screwed into the center electrode 31, to fasten the working head 10A, the electrode circuit board 39, and the center electrode 31. The ring electrode, the first group of electrodes, and the second group of electrodes all may be fixedly connected to the electrode circuit board 39 by using the fastener. In some other embodiments, the ring electrode and the second first group of electrodes may be fixedly connected to the electrode circuit board 39 by using the fastener. The second group of electrodes is only fixedly connected to the working head 10A by using the fastener, and the connection protrusion part 301 and the positioning protrusion pillar 302 in the second group of electrodes may be inclined relative to the working surface 110, to facilitate mounting and fastening by using the fastener.

It is noted herein that the fastener used to connect the electrode to the working head 10A may be of a conductive material, and can transmit a current to the electrode or receive a current of the electrode.

In some embodiments, with reference to FIG. 1, an area of the working surface 110 ranges from 6 square centimeters to IS square centimeters, for example, may be 6, 8, 10, 12, 13, or 15 square centimeters. It is noted herein that the area of the working surface 110 is an overall area surrounded by an outer periphery of the working surface 110. Through such disposition, the area of the working surface 110 is large, so that a large quantity of electrodes 30 can be disposed.

In some embodiments, with reference to FIG. 4, an included angle between the working surface 110 and the length direction A1 is less than or equal to 45 degrees, for example, may be 45 degrees, 42 degrees, 40 degrees, 38 degrees, 35 degrees, 32 degrees, 30 degrees, 25 degrees, 20 degrees, 18 degrees, 15 degrees, or 10 degrees. Further, the included angle between the working surface 110 and the length direction A1 may be set to be greater than or equal to 15 degrees and less than or equal to 40 degrees. Still further, the included angle between the working surface 110 and the length direction A1 may be set to be greater than or equal to 18 degrees and less than or equal to 35 degrees.

It may be understood that when the beauty instrument 100 works, the user holds the housing with the left hand or the right hand, so that the working surface is attached to the to-be-treated skin on the face of the user. When the included angle between the working surface 110 and the length direction A1 is larger, the hand of the user needs to be lifted higher. This easily leads to fatigue. However, if the included angle is smaller, an included angle between the working surface and a front side surface of the front side panel is prone to be smaller. This is not conducive to attaching the working surface 110 to the skin. In this application, the included angle between the working surface 110 and the length direction A1 may be set to be less than or equal to 40 degrees and greater than or equal to 15 degrees. This can prevent the user from lifting the hand excessively high, and can also facilitate attachment of the working surface to the skin.

In addition, the included angle between the working surface 110 and the length direction A1 is set to be less than or equal to 40 degrees, so that the working surface 110 can have a large area. It is easy to understand that if the included angle is smaller, the area of the formed working surface 110 is larger.

In addition, in this application, the front side panel is designed as an arc-shaped panel, an upper end thereof is bent forward, and the included angle between the working surface and the length direction A1 is less than or equal to 45 degrees, so that an included angle between the working surface and the upper end of the front side surface of the front side panel can be large, to facilitate attachment of the working surface to the skin.

In some embodiments, with reference to FIG. 1, FIG. 2, and FIG. 4, the housing 10 includes a handheld segment 10D and an expansion segment 10E from the tail 101 to the head 102. In a direction gradually away from the tail 101, that is, in a direction from the tail 101 of the housing to the head 102, a speed at which the distance between the front-side protection panel 12 and the inner housing back cover 13 in the handheld segment 10D increases is less than a speed at which the distance between the front-side protection panel 12 and the inner housing back cover 13 in the expansion segment 10E increases. A cross-sectional size of the handheld segment 10D may be constant or gradually increase in the direction gradually away from the tail 101, to facilitate holding by the user with the hand. A cross-sectional size of the expansion segment 10E is set to gradually increase in the direction gradually away from the tail 101. Correspondingly, the distance in the handheld segment 10D is set to be unchanged or slightly changed, to facilitate holding by the user. The distance in the expansion segment 10E increases rapidly, so that large internal space is easily obtained, to mount an internal component. In addition, the area of the working surface 110 increases easily.

In some embodiments, with reference to FIG. 1, FIG. 2, and FIG. 4, the distance between the front-side protection panel 12 and the inner housing back cover 13 in the handheld segment OD remains unchanged. Therefore, the distance in the handheld segment 10D remains unchanged, to facilitate holding by the user, and facilitate structural design and manufacture. In some other embodiments, the distance between the front-side protection panel 12 and the inner housing back cover 13 in the handheld segment 10D may also slightly increase in the direction gradually away from the tail 101. For example, a ratio of a maximum distance between the front-side protection panel 12 and the inner housing back cover 13 in the handheld segment 10D to a minimum distance between the front-side protection panel 12 and the inner housing back cover 13 in the handheld segment 10D may be in a range of 1.2:1 to 1:1.

In some embodiments, with reference to FIG. 1 to FIG. 4, a width of the front side panel such as the front-side protection panel 12 and/or the front cover 16 in the handheld segment 10D remains unchanged, and the width of the front side panel such as the front-side protection panel 12 and/or the front cover 16 in the expansion segment 10E gradually decreases in a direction gradually close to the head 102.

In some embodiments, with reference to FIG. 1, FIG. 2, and FIG. 4, an overall bending degree of the handheld segment 10D is less than an overall bending degree of the expansion segment 10E. As shown in FIG. 4, the overall bending degree herein is a degree at which center lines of the handheld segment 10D and the expansion segment 10E are bent towards the front side of the beauty instrument 100 or curvature of the center line. The overall bending degree of the handheld segment 10D is set to be small, that is, the handheld segment is straight as a whole. This also facilitates holding by the user.

In some embodiments, with reference to FIG. 1 to FIG. 4 and FIG. 22, FIG. 22 is a schematic three-dimensional diagram of a back cover and a handle of a beauty instrument according to some embodiments of this application. The rear side surface 170 includes a curved surface part 171 that conforms to ergonomics, and the handle 20 divides the curved surface part 171 into a palm holding part 172 and a finger touching part 173. The palm holding part 172 is located between the handle 20 and the tail 101, and is configured to fit the palm part of the user when the user grips the handle 20 with two fingers. The finger touching part 173 is located between the handle 20 and the head 102, and is configured to fit the finger part of the user when the user grips the handle 20 with two fingers. A bending amplitude of the finger touching part 173 is greater than a bending amplitude of the palm holding part 172. The curved surface part 171 may include an arc-shaped surface or a spherical surface. Through such disposition, the curved surface part 171 included in the rear side surface 170 can conform to natural bending degree distribution when the hand part holds the beauty instrument 100 by griping the handle 20, to match a palm surface of the palm of the user, thereby improving comfort during operation. It is noted herein that the description of the rear side surface 170 herein is also applicable to the inner housing back cover 13. In other words, a rear side surface of the inner housing back cover 13 may have a same feature as the rear side surface 170.

Figure 23:
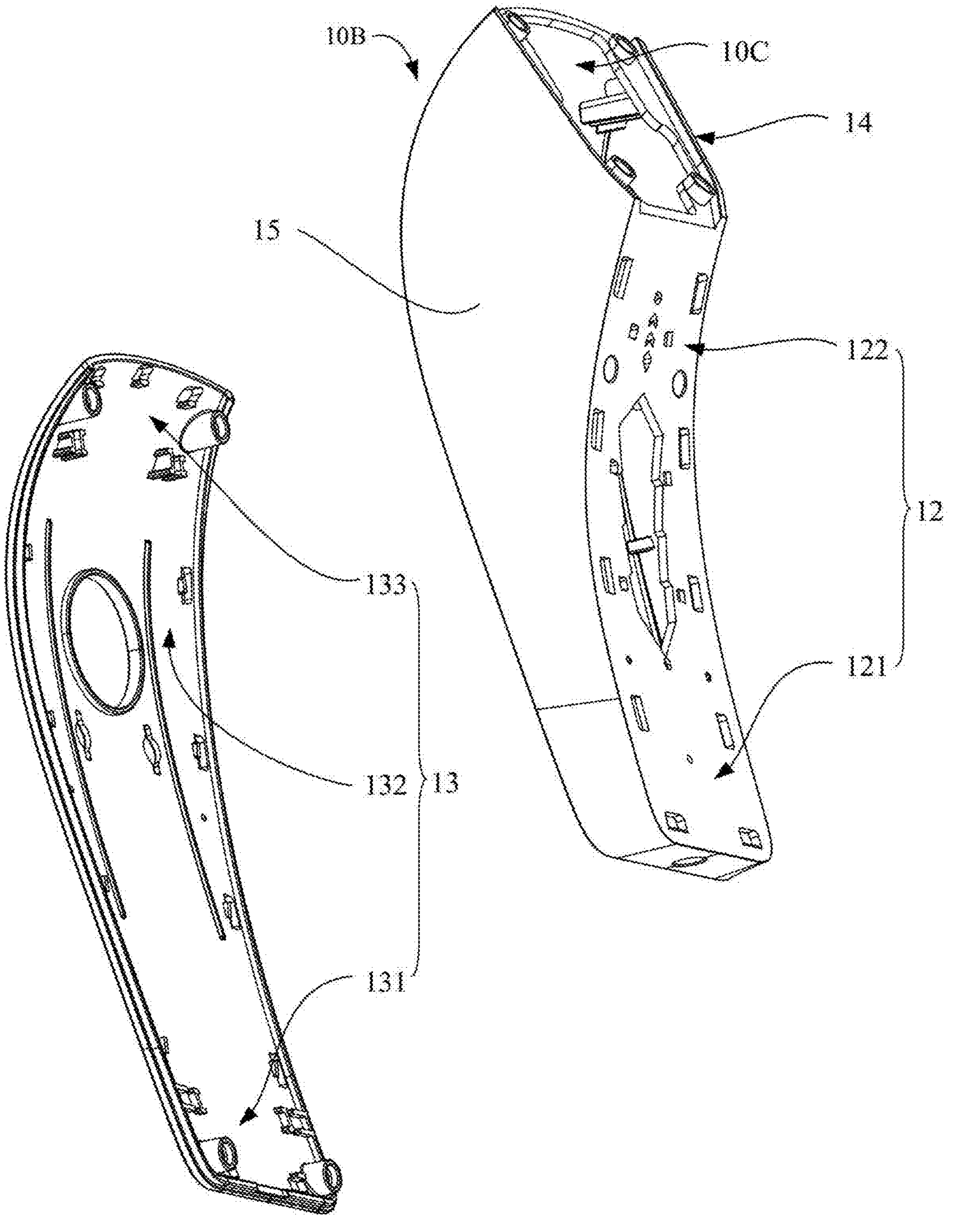
FIG. 23 is a schematic three-dimensional exploded view of a housing body of the beauty instrument shown in FIG. 1.

In some embodiments, with reference to FIG. 3, FIG. 4, and FIG. 23, FIG. 23 is a schematic three-dimensional exploded view of a housing body of the beauty instrument shown in FIG. 1. The housing body 10B includes the front-side protection panel 12, and the inner housing back cover 13 is mounted on the housing body 10B. The front side panel such as the front-side protection panel 12 includes a first handheld part 121 and a first expansion part 122, and the first expansion part 122 is bent and extends forward from an upper end of the first handheld part 121, so that an upper end of the first expansion part 122 protrudes forward in the thickness direction A3 from the first handheld part 121 of the front-side protection panel 12. In this manner, the speed at which the distance between the front-side protection panel 12 and the inner housing back cover 13 in the handheld segment 10D increases is less than the speed at which the distance between the front-side protection panel 12 and the inner housing back cover 13 in the expansion segment 10E increases.

Further, in the direction gradually away from the tail 101, a slope by which the first expansion part 122 is inclined forward may gradually increase, or at least partially increase gradually. In this manner, in the direction gradually away from the tail 101, the distance between the front-side protection panel 12 and the inner housing back cover 13 can gradually increase.

In some embodiments, with reference to FIG. 3, FIG. 4, and FIG. 23, the inner housing back cover 13 includes a second handheld part 131, a second expansion part 132, and an extension part 133 that are successively connected. An upper end of the second expansion part 132 and the upper end of the front-side protection panel 12 are flush in the length direction A1. In other words, the top of the second expansion part 132 and the top of the front-side protection panel 12 are flush in the length direction A1. The extension part 133 is disposed at the upper end of the second expansion part 132, and is bent and extends forward.

The first handheld part 121, the first expansion part 122, the second handheld part 131, the second expansion part 132, and the extension part 133 are disposed in this manner, so that a structure that facilitates holding by the user and that can increase the area of the working surface 110 can be implemented.

Figure 24:
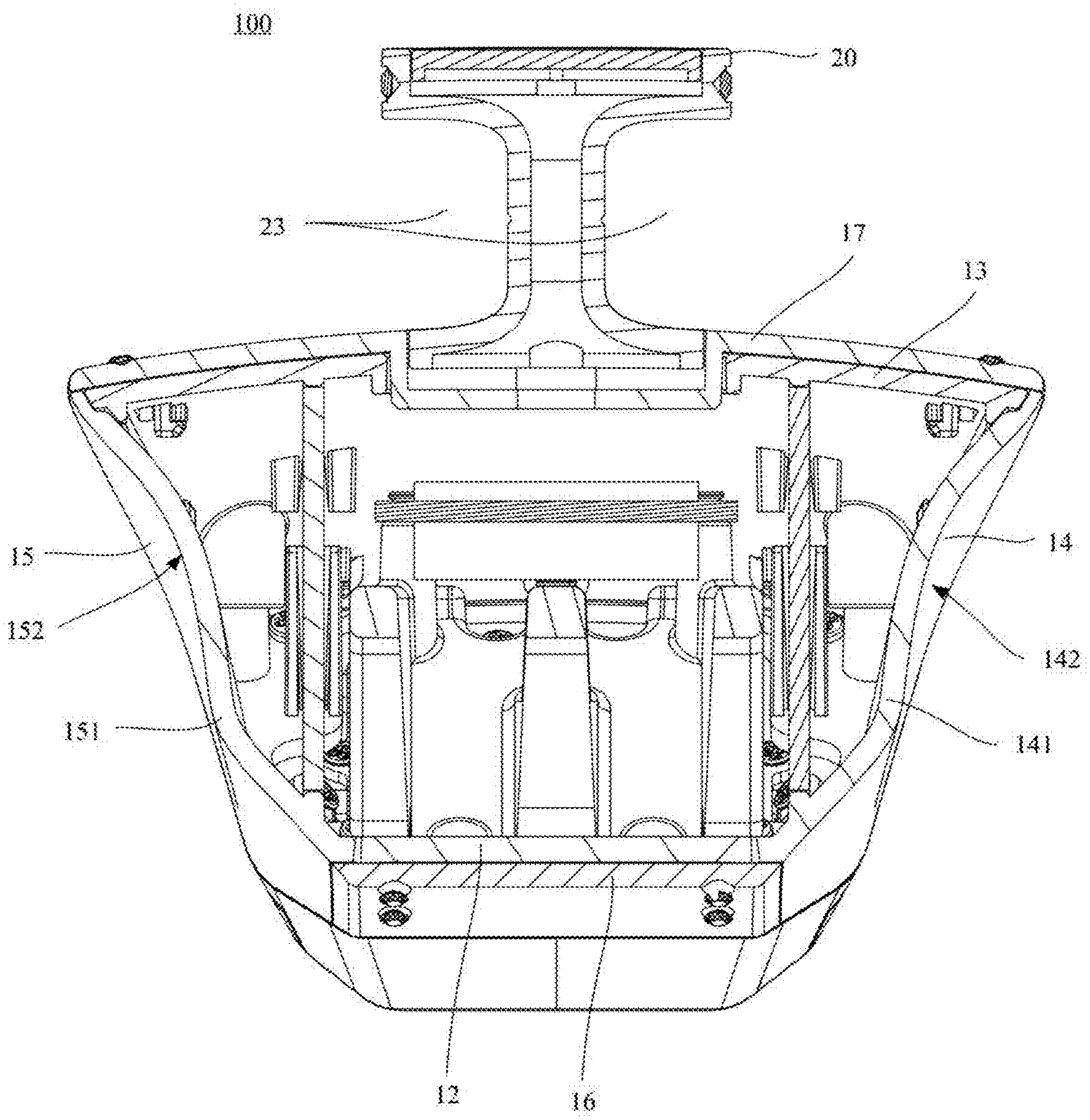
FIG. 24 is a schematic sectional view of the beauty instrument shown in FIG. 2 along B-B.

In some embodiments, with reference to FIG. 1 and FIG. 24, FIG. 24 is a schematic sectional view of the beauty instrument shown in FIG. 2 along B-B. A convex part 141 that extends in the length direction A1 is disposed on the left side panel 14, and a convex part 151 that extends in the length direction A1 is disposed on the right side panel 15. These convex parts 141 and 151 may be structures that protrude outward relative to the left side panel 14 and the right side panel 15, and may be linear or curved, but generally extend in the length direction A1. A concave part 142 is formed between the convex part 141 and the inner housing back cover 13 for grip by a finger. A concave part 152 is formed between the convex part 151 and the inner housing back cover 13 for grip by a finger. The bottom of the concave part 152 is concave to the other side, that is, the bottom of the concave part 142 of the left side panel 14 is concave to the right, and the bottom of the concave part 152 of the right side panel 15 is concave to the left.

In some other embodiments, with reference to FIG. 1 and FIG. 24, concave parts 142 and 152 may be disposed on the left side panel 14 and/or the right side panel 15, but the convex parts 141 and 151 are not disposed, and the concave parts 142 and 152 may also be used for grip by a finger.

In these embodiments, the concave parts 142 and 152 are disposed, so that it is convenient for a finger of the user to grip/press the concave parts 142 and 152, thereby increasing holding strength of the user for the beauty instrument 100 and comfort thereof. For example, when the user presses the inner housing back cover 13 with the right hand, the thumb of the user may press the concave part 142, and the little finger thereof may press the concave part 152.

In some embodiments, with reference to FIG. 1 and FIG. 24, the convex part 151 may have a highest part in the length direction, and a height thereof gradually decreases separately upward and downward from the highest part. The highest part may be located in a middle position of the convex part 151. The convex part 141 may have a same structure as the convex part 151. In this manner, a deep concave part may be formed between the highest parts of the convex parts 141 and 151 and the inner housing back cover 13, so that the thumb and the little finger of the user can press the deep concave part.

In some embodiments, with reference to FIG. 1 to FIG. 3, at least in a middle part 103 between the head 102 and the tail 101, a width of the rear side panel such as the inner housing back cover 13 is greater than a width of the front side panel such as the front-side protection panel 12. Alternatively, from the head 102 to the tail 101, a width of the inner housing back cover 13 is greater than a width of the front-side protection panel 12. The width is a size in the width direction A2 perpendicular to the length direction A1. The width of the inner housing back cover 13 is greater than the width of the front-side protection panel 12, so that a structure with narrow front and wide back can be formed, to facilitate holding by the user, and better conform to ergonomic design.

In some embodiments, with reference to FIG. 1 and FIG. 24, the highest parts of the convex parts 141 and 151 or relatively high segments in the middle of the convex parts 141 and 151 correspond to the handle 20. In this manner, when the user grips the handle 20 with two fingers, the thumb and the little finger of the user can conveniently press the deep concave part.

In some embodiments, with reference to FIG. 1, FIG. 2, and FIG. 24, the convex parts 141 and 151 may be located in the expansion segment 10E. In other words, the convex parts 141 and 151 may be disposed only in the expansion segment 10E. The concave parts 142 and 152 formed between the convex parts 141 and 151 and the rear side panel may cooperate with the handle 20, so that the user can control and operate the beauty instrument 100. Because the handheld segment 10D is configured to be held by the user with the hand, the convex parts 141 and 151 do not need to be disposed on the left side panel 14 and/or the right side panel 15 corresponding to the handheld segment 10D.

Figure 22:
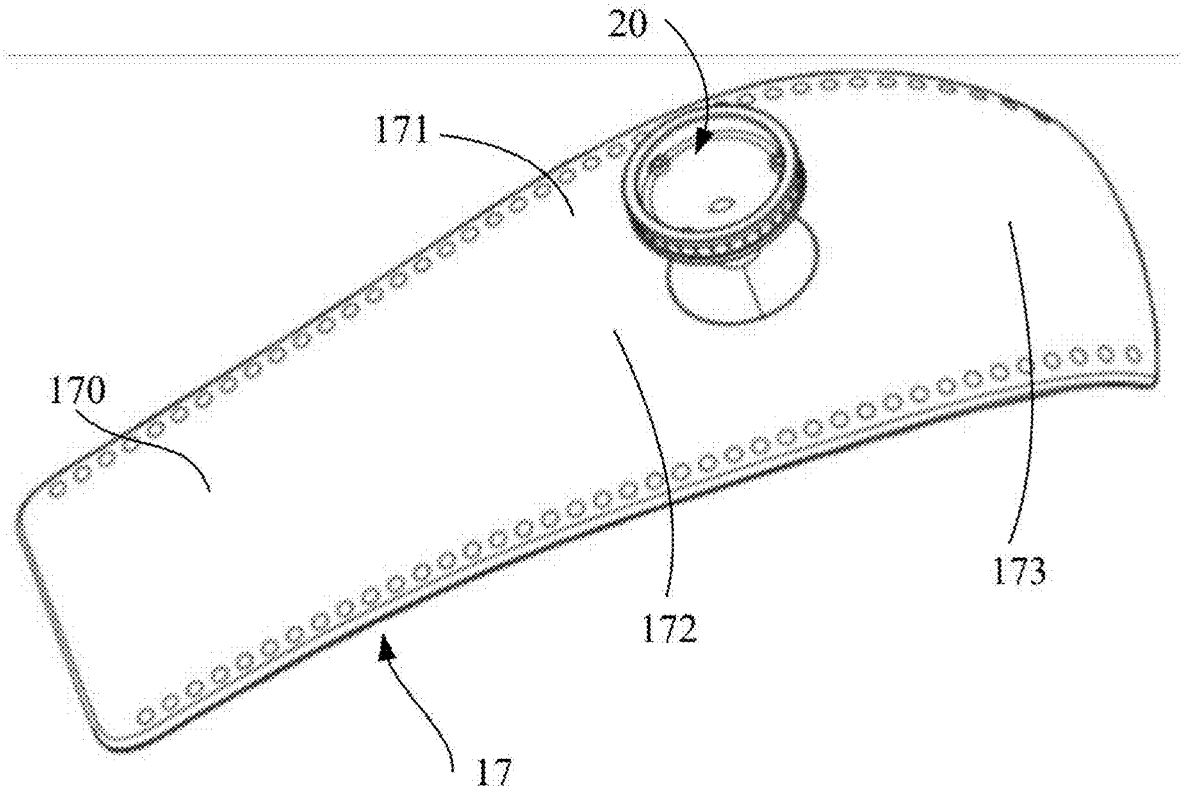
FIG. 22 is a schematic three-dimensional diagram of a back cover and a handle of a beauty instrument according to some embodiments of this application.

In some embodiments, with reference to FIG. 22 and FIG. 23, when the beauty instrument 100 does not include the back cover 17, but includes the inner housing back cover 13, the rear side surface 170 may be located on the inner housing back cover 13. Correspondingly, the second expansion part 132 of the inner housing back cover 13 may include a palm holding part 172, and the extension part 133 may include a part of the finger touching part 173.

In some embodiments, with reference to FIG. 4 and FIG. 22, an included angle between the finger touching part 173 and the working surface 110 is less than 90 degrees, for example, may be 89 degrees, 85 degrees, 80 degrees, 75 degrees, 70 degrees, or 60 degrees. An included angle between the front-side protection panel 12 and the working surface 110 is greater than 90 degrees, for example, may be 95 degrees, 98 degrees, 100 degrees, 105 degrees, 110 degrees, or 120 degrees. Through such disposition, an inclined structure of the working surface 110 can be easily implemented, thereby increasing an area of the working surface 110.

In some embodiments, with reference to FIG. 4 and FIG. 22, a length of the palm holding part 172 is greater than a length of the finger touching part 173. The length may be a size in a direction from the tail 101 to the head 102. Through such disposition, it can be convenient for the user to hold the beauty instrument 100, and the palm holding part 172 has a large length, and may also be directly held by the user, to implement a mobile operation in a plurality of manners.

In some embodiments, with reference to FIG. 3 and FIG. 24, a width of the front-side protection panel 12 is less than a width of the inner housing back cover 13, a width of the inner housing back cover 13 in which the handle 20 is located is greater than a width of the palm holding part 172, and the width of the inner housing back cover 13 in which the handle 20 is located is greater than a width of the finger touching part 173. Because the inner housing back cover 13 is a side for operation by the user with the palm, a width of the inner housing back cover 13 is set to be larger than a width of the front-side protection panel 12. In this way, it is convenient for operation by the user. In addition, a size of the entire beauty instrument 100 is avoided being large, so that the entire beauty instrument 100 still presents a compact outline.

In an embodiment including the back cover 17 and the front cover 16, as shown in FIG. 2, at least at an end close to the working surface 110, a width of the back cover 17 in the width direction A2 perpendicular to the length direction A1 is greater than a width of the front cover 16. For example, near a position at which the handle 20 is disposed, the width of the back cover 17 may be greater than the width of the front cover 16. In this embodiment, the width of the back cover 17 on which the handle 20 is mounted is set to be greater than the width of the front cover 16, so that an area of the back cover 17 can be increased, thereby helping the palm of the user be in contact with and hold the back cover 17. Correspondingly, as shown in FIG. 3, an overall shape of the inner housing back cover 13 is similar to an overall shape of the back cover 17, and an overall shape of the front cover 16 is similar to an overall shape of the front-side protection panel 12.

In some embodiments, with reference to FIG. 3, FIG. 4, and FIG. 9, a cold compress member 51 is inserted into a center position of the top panel 11 of the beauty instrument 100, and the electrode 30 may include a center electrode 31, an upper electrode 32, a right electrode 33, a lower electrode 34, a left electrode 35, an upper edge electrode 36, a left edge electrode 37, and a right edge electrode 38. The center electrode 31 is disposed on the working surface 110 and surrounds the cold compress member 51, the upper electrode 32, the right electrode 33, the lower electrode 34, and the left electrode 35 are disposed on the working surface 110 and surround the center electrode 31, the upper edge electrode 36 is disposed on an upper edge of the top panel 11, and the left edge electrode 37 and the right edge electrode 38 are respectively disposed on a left edge and a right edge of the top panel 11.

The beauty instrument 100 may further include an electrode circuit board 39. The center electrode 31, the upper electrode 32, the right electrode 33, the lower electrode 34, the left electrode 35, the upper edge electrode 36, the left edge electrode 37, and the right edge electrode 38 may be connected to the electrode circuit board 39. One or more electrode circuit boards 39 may be disposed.

These electrodes are approximately evenly distributed on the working surface 110, to perform even care on the skin of the user. In addition, these electrodes are disposed on the working surface 110 with a large area, so that a skin area in each time of care can be increased, to improve working efficiency of the beauty instrument 100, and save time for the user. Different electrodes may work independently or together. Different treatment manners are used for different skin parts, for example, radio frequency beauty treatment or microcurrent beauty treatment, and corresponding working modes and output energy may also be different.

In an embodiment, the center electrode 31, the upper electrode 32, the right electrode 33, the lower electrode 34, and the left electrode 35 may be optionally RF electrodes to output RF energy, such as dynamic energy output of variable-frequency RF ranging from 0.5 MHz to 3.0 MHz.

In this way, the upper electrode 32, the right electrode 33, the lower electrode 34, and the left electrode 35 are disposed around the center electrode 31, so that star-ring electrode arrangement can be implemented, and a surging energy field can be implemented.

In an embodiment, the upper edge electrode 36, the left edge electrode 37, and the right edge electrode 38 may be optionally EMS electrodes to output a microcurrent.

In this way, these electrodes cooperate with the center electrode 31, the upper electrode 32, the right electrode 33, the lower electrode 34, and the left electrode 35, to implement 8-pole star-ring electrodes with hurricane-like empowerment, implement densely release microcurrents in a hurricane belt-like manner, implement comfortable suction for lifting and shaping, and implement one-side V-face lifting in 3 minutes.

In this way, through circuit control, effects such as deep skin penetration, collagen activation, lifting and tightening of the skin, brightening of the skin, reducing of wrinkles, and lifting and shaping can be achieved.

In an experiment, the beauty instrument in this application can reduce forehead lines by 15%, under-eye lines by 25%, crow's feet by 30%, and nasolabial folds by 20%. After four weeks of continuous use, the entire face is firmer and more elastic, skin firmness is increased by 15.7%, and skin elasticity is increased by 12.7%.

Figure 17:
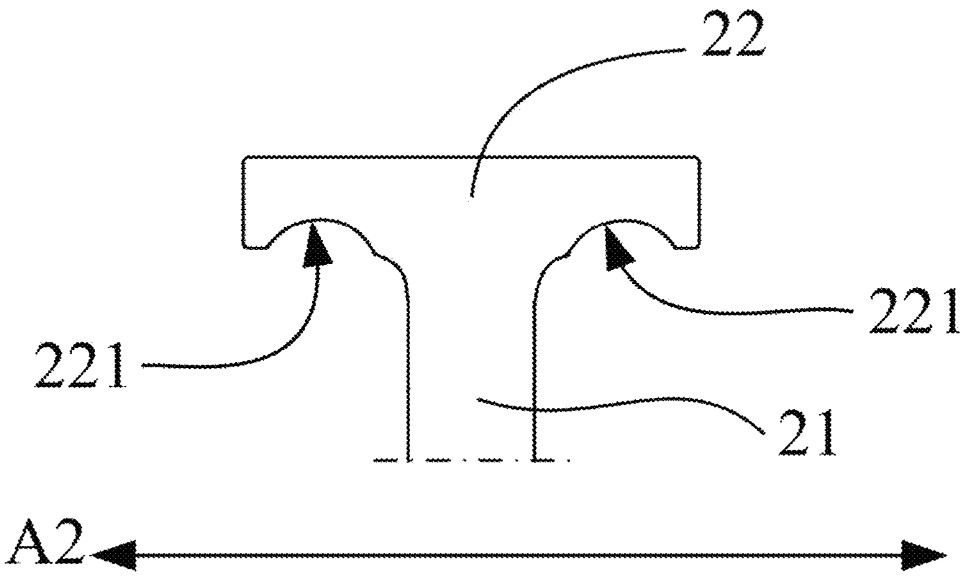
FIG. 17 is a schematic planar diagram of a handle of a beauty instrument according to some embodiments of this application.

In some embodiments, with reference to FIG. 2 and FIG. 17, two first grooves 221 are disposed on a side surface that is of the blocking part 22 and that faces the rear side surface 170, and the two first grooves 221 are configured to accommodate a finger of the user, and are respectively located on both sides of the connection pillar 21 in the width direction A2 of the housing 10. In other words, the two first grooves 221 may be disposed on the left and right sides of the blocking part 22. Further, each of the two first grooves 221 has one extension direction, and the two extension directions of the two first grooves 221 form an included angle. The included angle may be consistent with or substantially consistent with an included angle formed when two fingers of the user grip the connection pillar 21. In other words, a distance between the two first grooves 221 may gradually increase in a direction gradually close to the working surface 110. For example, if the included angle formed when the two fingers of the user grip the connection pillar 21 generally falls within a range of 5 degrees to 20 degrees, the included angle between the two first grooves 221 may also be set to fall within a range of 5 degrees to 20 degrees, for example, 5 degrees, 8 degrees, 10 degrees, 15 degrees, 17 degrees, or 20 degrees. A width of the first groove 221 may be close to a width of the finger of the human body. Therefore, the two first grooves 221 are disposed, so that it can be convenient for the finger of the user to be partially accommodated in the groove, a feature that an included angle exists when two adjacent fingers are open and grip the connection pillar 21 can be matched, and it is not easy to cause discomfort to the finger.

Figure 18:
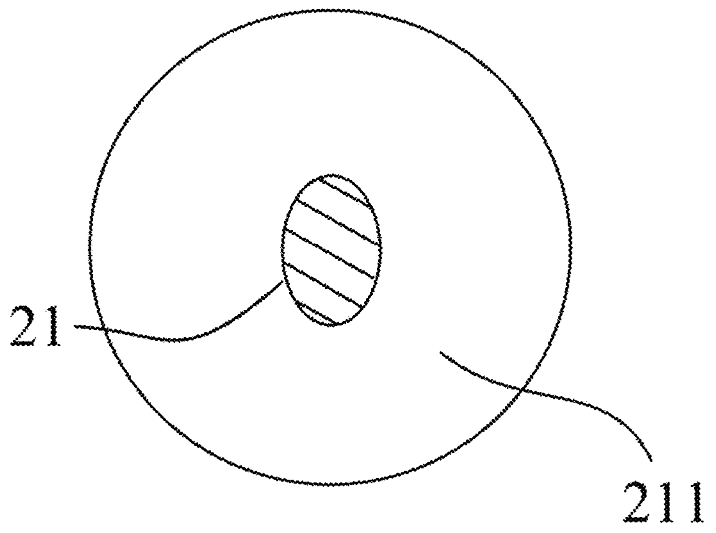
FIG. 18 is a schematic sectional view of a handle of a beauty instrument according to some embodiments of this application.

In some embodiments, with reference to FIG. 2 and FIG. 18, the connection pillar 21 has an elliptical columnar structure. In other words, a cross-section of the connection pillar 21 may be elliptical. In some other embodiments, the connection pillar 21 may include a cylindrical structure. It is easy to understand that, the elliptical columnar structure is disposed, so that it can be convenient for the user to grip the connection pillar 21 with fingers, and it is not easy to cause discomfort to the fingers.

Figure 19:
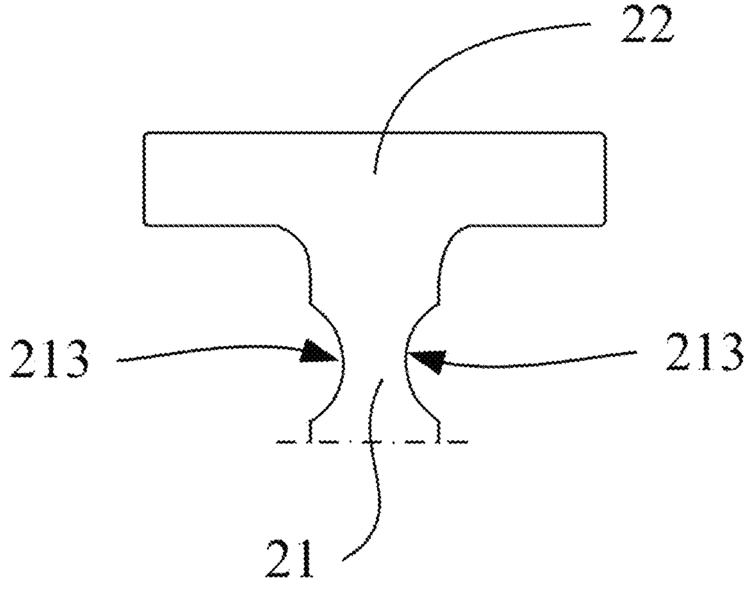
FIG. 19 is a schematic planar diagram of a handle of a beauty instrument according to some embodiments of this application.

In some other embodiments, with reference to FIG. 2 and FIG. 19, two opposite second grooves 213 are disposed on a peripheral surface of the connection pillar 21, and the two second grooves 213 are configured to accommodate a finger of the user, and are respectively located on both sides of the connection pillar 21 in the width direction A2 of the housing 10. In other words, the two second grooves 213 may be disposed on the left and right sides of the connection pillar 21. In other words, when the user grips the connection pillar 21 with two fingers, parts that are of the two fingers and that are close to each other may be accommodated in the second groove 213. Further, each of the two second grooves 213 has one extension direction, the two extension directions of the two second grooves 213 form an included angle, and the included angle may be consistent with or substantially consistent with an included angle formed when two fingers of the user grip the connection pillar 21. In other words, a distance between the two second grooves 213 may gradually increase in a direction gradually close to the working surface 110. For example, the included angle between the two second grooves 213 may be set to fall within a range of 5 degrees to 20 degrees, for example, 5 degrees, 8 degrees, 10 degrees, 15 degrees, 17 degrees, or 20 degrees. Correspondingly, the second groove 213 is disposed, so that it can be convenient for the user to grip the connection pillar 21 with fingers, and it is not easy to cause discomfort to the fingers.

In some embodiments, with reference to FIG. 2, a cushion (not shown in the figure) may be disposed on the peripheral side surface and/or the rear side surface 170 of the connection pillar 21. The cushion may be made of a material with lower hardness than the connection pillar 21 and/or the housing 10, such as rubber or leather. The cushion is disposed, so that extrusion on the finger of the user by the hard material can be reduced, thereby improving user comfort during use.

In some embodiments, the beauty instrument 100 may include a cushion and the foregoing two first grooves 221 and/or the foregoing two second grooves 213. For example, a cushion may be disposed in the first groove 221, so that the cushion adaptively forms a concave part for accommodating the finger of the user. Similarly, a cushion may be disposed in the second groove 213, so that the cushion adaptively forms a concave part for accommodating the finger of the user. Therefore, user comfort during use may be further improved.

In some embodiments, FIG. 20 is a schematic three-dimensional diagram of a handle of a beauty instrument according to this application. The connection pillar 21 includes a first trigger part 215 and a second trigger part 216, and the first trigger part 215 and the second trigger part 216 are opposite to each other. The beauty instrument 100 is configured to enable a working state only when the first trigger part 215 and the second trigger part 216 are simultaneously in contact with the finger. The first trigger part 215 and the second trigger part 216 may be of electrically conductive materials, and are disposed to be connected to a control circuit of the beauty instrument. The first trigger part 215 and the second trigger part 216 are disposed. In this way, when the user starts to use the beauty instrument 100 such as a beauty instrument, the fingers grip the handle 20 and are simultaneously in contact with the first trigger part 215 and the second trigger part 216, and then trigger the beauty instrument 100 to start working. After the user completes the use, and the fingers leave and do not grip the handle 20, the beauty instrument 100 automatically turns off, thereby improving convenience of use. In addition, because the two contacts such as the first trigger part 215 and the second trigger part 216 are generally hidden under the blocking part 22 of the handle 20, the two contacts are not easily triggered accidentally.

Figure 21:
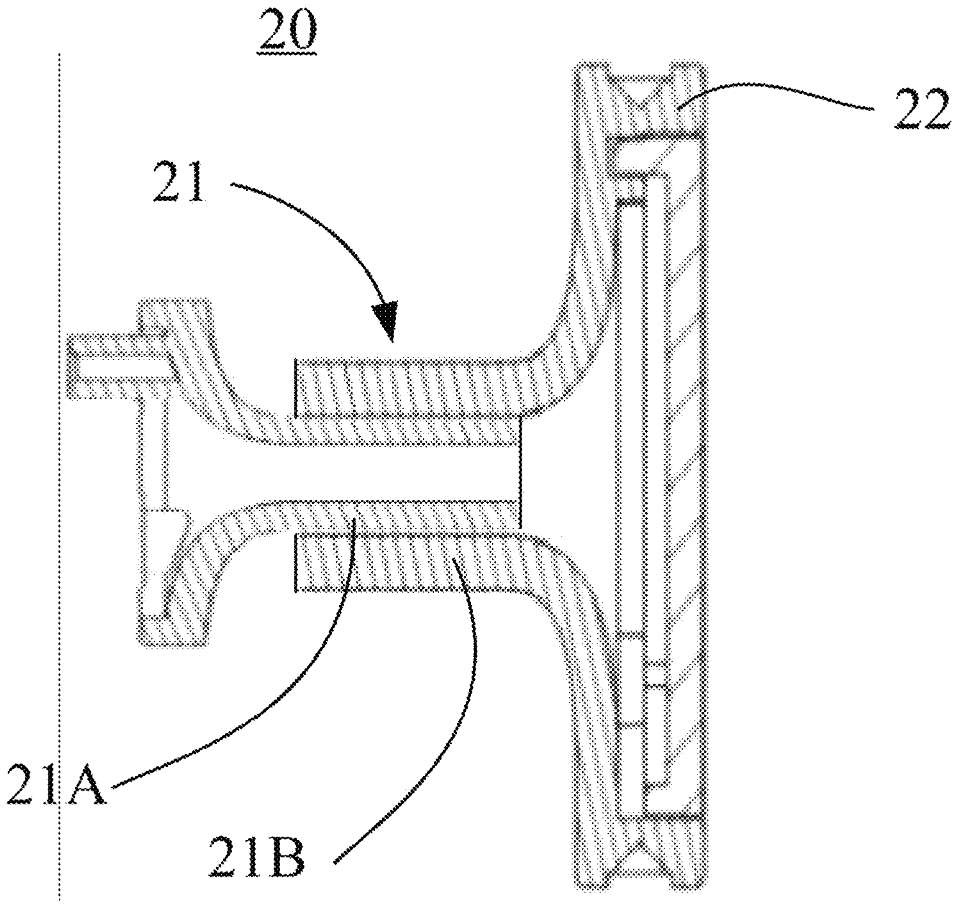
FIG. 21 is a schematic sectional view of a handle of a beauty instrument according to some embodiments of this application.

In some embodiments, with reference to FIG. 2 and FIG. 21, FIG. 21 is a schematic sectional view of a handle of a beauty instrument according to this application. The connection pillar 21 includes a first connection pillar 21A and a second connection pillar 21B, the first connection pillar 21A is connected to the housing 10, the second connection pillar 21B is connected to the blocking part 22, and the second connection pillar 21B is configured to rotate relative to the first connection pillar 21A. In this embodiment, the connection pillar 21 is divided into two parts, the second connection pillar 21B may be considered as a knob connected to the first connection pillar 21A, and contact surfaces between the first connection pillar 21A and the second connection pillar 21B may be disposed as different parts, thereby adjusting a range or switching a beauty mode when the second connection pillar 21B is rotated. For example, one or more contacts may be disposed on an outer side surface of the first connection pillar 21A, and one or more contacts may be disposed on an inner side surface of the second connection pillar 21B. When one contact of the second connection pillar 21B is in contact with one contact of the first connection pillar 21A, the beauty instrument has a corresponding range or mode. When another contact of the second connection pillar 21B is in contact with another contact of the first connection pillar 21A, the beauty instrument has another corresponding range or mode.

With reference to FIG. 3 and FIG. 4, the following briefly describes an assembly process of main components of the beauty instrument 100 in this embodiment of this application. In a first step, waterproof O-rings are placed in screw holes formed on the working head 10A, and these screw holes are located at a position of the to-be-mounted electrode 30 of the working head 10A. In a second step, a threaded pillar on a side that is of the electrode 30 and that faces the working surface 110 is inserted into the screw hole, and the electrode 30 is fastened to the working head 10A through interference fit assembly between the threaded pillar and the waterproof O-ring, where the electrode 30 is exposed to the working surface 110. In a third step, the cold compress member 51 such as a sapphire is mounted on the working head 10A. In a fourth step, the electrode circuit board 39 is placed on an inner side of the working head 10A, the electrode circuit board 39 is fastened to the working head 10A by using a screw, and the electrode 30 is fastened by using a screw. In a fifth step, the button 62 is mounted on the front-side protection panel 12 of the housing body 10B, the button 62 is fastened by using a hot melt pole, and the button light guide member 63 is mounted at the button 62. In a sixth step, the working head 10A on which the cold compress member 51 and the electrode 30 are mounted is combined with the housing body 10B, and the working head 10A and the housing body 10B are fastened by using a screw. In a seventh step, one piece of thermally conductive silicone and the refrigeration member 52 are successively disposed on the mounting protrusion part 42 of the heat dissipation member 40. In an eighth step, another piece of thermally conductive silicone is disposed on the conduction surface 512 of the cold compress member 51 on the working head 10A. In a ninth step, the heat dissipation member 40 on which the refrigeration member 52 is mounted and the working head 10A are assembled together, and the heat dissipation member 40 and the working head 10A may be fastened by using a screw. In a tenth step, the main control circuit board 71 is mounted on the heat dissipation member

40, and the main control circuit board 71 and the heat dissipation member 40 may be fastened by using a screw. In an eleventh step, the left support panel 18 and the right support panel 19 are respectively inserted into the left and right sides of the housing body 10B, and are disposed to be substantially perpendicular to the heat dissipation member 40. In a twelfth step, the main control circuit board 71 is connected to the electrode circuit board 39 by using a flat cable. In a thirteenth step, the charging interface 81 is mounted, and may be fastened to the tail of the housing body 10B by using a screw. In a fourteenth step, the inner housing back cover 13 is mounted, and may be fastened to the housing body 10B by using a screw. In a fifteenth step, the handle 20 is fastened to the back cover 17 by using a screw. In a sixteenth step, the back cover 17 is snapped onto the inner housing back cover 13. In a seventeenth step, the front cover 16 and the decorative button panel 64 are snapped onto the front-side protection panel 12.

In this application, a light therapy lamp such as an LED lamp may further be disposed on the electrode circuit board 39. There are a plurality of light therapy lamps that are distributed in a ring shape. The plurality of light therapy lamps are disposed around the center electrode 31. Because the working head of the product is large, 18 to 25 light therapy lamp beads may be disposed.

Optionally, the light therapy lamp is configured to emit red light with a wavelength of 620 nanometers to 640 nanometers (for example, optionally a 620-nanometer, 625-nanometer, or 630-nanometer light), to implement skin softening.

In this application, the beauty instrument 100 can implement intelligent transient red light, soften the skin, and reduce wrinkles.

It is noted herein that some features in the beauty instrument 100 in this application may be applied to a skin treatment apparatus. For example, the beauty instrument 100 in this application may be used as a skin treatment apparatus without disposing the electrode 30, that is, the cold compress member 51 in the beauty instrument is configured to treat the skin of the user. In addition, a hair removal component may be added to use the beauty instrument 100 in this application as a hair removal instrument.

The beauty instrument in this application uses a gold super applicator head (gold electrode), so that external cooling and internal heating (icy sensation at the skin and heating on the dermis), powerful anti-aging effects with an extra-large applicator head (large electrode), and ice radio frequency without sensitivity can be implemented.

The foregoing descriptions are merely embodiments of this application, and are not intended to limit the patent scope of this application. Any equivalent structure or equivalent process transformation that is made according to the content in the specification and the accompanying drawings of this application, or an application of the content in the specification and the accompanying drawings of this application directly or indirectly to another related technical field, shall fall within the protection scope of this application.

What is claimed is:

1. A beauty instrument, comprising: a housing (10), wherein the housing (10) comprises a working head (10A); and an electrical stimulation component, wherein the electrical stimulation component comprises an EMS stimulation circuit (72), an RF radio frequency circuit (73), and a ring electrode, a first group of electrodes, and a second group of electrodes that are all disposed on the working head (10A), the ring electrode is separately connected to the EMS stimulation circuit (72) and the RF radio frequency circuit (73), the first group of electrodes comprises a plurality of first electrodes, the plurality of first electrodes are all connected to the RF radio frequency circuit (73) and/or connected to the EMS stimulation circuit (72), the plurality of first electrodes are distributed at intervals around the ring electrode, the second group of electrodes comprises a plurality of second electrodes, the plurality of second electrodes are all connected to the EMS stimulation circuit (72), and the plurality of second electrodes are distributed at intervals around the first group of electrodes; the beauty instrument (100) further comprises a cold compress member (51), the cold compress member (51) comprises a transparent crystal mounted on the working head (10A), and the ring electrode is disposed around the transparent crystal, the EMS stimulation circuit is an Electrical Muscle Stimulation stimulation circuit.

2. The beauty instrument according to claim 1, wherein the ring electrode is in a quadrilateral ring shape, the plurality of first electrodes comprises four first electrodes, and the four first electrodes each correspond to one edge of the ring electrode.

3. The beauty instrument according to claim 1, wherein the ring electrode is in a quadrilateral ring shape, the plurality of second electrodes comprises three second electrodes, and the three second electrodes each correspond to one of three edges of the ring electrode.

4. The beauty instrument according to claim 1, wherein the ring electrode is in a quadrilateral ring shape, the plurality of first electrodes comprises four first electrodes, the four first electrodes each correspond to one edge of the ring electrode, and the four first electrodes are respectively an upper electrode (32), a right electrode (33), a lower electrode (34), and a left electrode (35); and there are three second electrodes, the three second electrodes each correspond to one of three edges of the ring electrode, the second electrodes are disposed at an edge of the working head (10A), and the three second electrodes are respectively an upper edge electrode (36), a left edge electrode (37), and a right edge electrode (38).

5. The beauty instrument according to claim 2, wherein the working head (10A) has a working surface (110) inclined to a length direction (A1) of the housing (10), the ring electrode and the first group of electrodes are mounted on the working surface (110), and an upper-side width of the working surface (110) is greater than a lower-side width; and the four first electrodes are respectively an upper electrode (32), a right electrode (33), a lower electrode (34), and a left electrode (35), a length of the upper electrode (32) is greater than a length of the lower electrode (34), and/or the upper electrode (32) is an arc-shaped electrode; and/or the ring electrode comprises an upper electrode edge and a lower electrode edge, and a length of the upper electrode edge is greater than a length of the lower electrode edge; and/or the ring electrode is disposed in a trapezoid shape or substantially in a trapezoid shape.

6. The beauty instrument according to claim 3, wherein the three second electrodes are respectively an upper edge electrode (36), a left edge electrode (37), and a right edge electrode (38), and the upper edge electrode (36) is an arc-shaped electrode.

7. The beauty instrument according to claim 2, wherein the ring electrode comprises an upper electrode edge, a left electrode edge, a right electrode edge, and a lower electrode edge, the four first electrodes are respectively an upper electrode (32), a right electrode (33), a lower electrode (34), and a left electrode (35), the plurality of second electrodes comprises three second electrodes, the second electrodes are disposed at an edge of the working head (10A), and the three second electrodes are respectively an upper edge electrode (36), a left edge electrode (37), and a right edge electrode (38); the upper electrode edge corresponds to the upper electrode (32) and the upper edge electrode (36), the left electrode edge corresponds to the left electrode (35) and the left edge electrode (37), the right electrode edge corresponds to the right electrode (33) and the right edge electrode (38), and the lower electrode edge corresponds to the lower electrode (34); and a distance between the upper electrode edge and the upper electrode (32) is greater than a distance between the upper electrode (32) and the upper edge electrode (36); and/or a distance between the left electrode edge and the left electrode (35) is greater than a distance between the left electrode (35) and the left edge electrode (37); and/or a distance between the right electrode edge and the right electrode (33) is greater than a distance between the right electrode (33) and the right edge electrode (38).

8. The beauty instrument according to claim 1, wherein the ring electrode, the first group of electrodes, and the second group of electrodes are mounted on the working head (10A) by using a fastener.

9. The beauty instrument according to claim 8, wherein at least one of the ring electrode, the first group of electrodes, and the second group of electrodes has a connection protrusion part (301), the working head (10A) is provided with a connection groove (114), and the connection protrusion part (301) is inserted into the connection groove (114), and the connection protrusion part (301) is fastened in the connection groove (114) by using the fastener.

10. The beauty instrument according to claim 9, wherein at least one of the ring electrode, the first group of electrodes, and the second group of electrodes has a positioning protrusion pillar (302), and the positioning protrusion pillar (302) is inserted into the working head (10A).

11. The beauty instrument according to claim 8, wherein the working head (10A) is provided with an accommodation groove (115), and at least one of the ring electrode, the first group of electrodes, and the second group of electrodes is accommodated by the accommodation groove (115); and/or the beauty instrument further comprises an electrode circuit board (39), the electrode circuit board (39) is disposed on a side that is of the working head (10A) and that faces away from the ring electrode, the first group of electrodes, and the second group of electrodes, and at least one of the ring electrode, the first group of electrodes, and the second group of electrodes is fixedly connected to the electrode circuit board (39) by using the fastener.

12. The beauty instrument according to claim 1, wherein the ring electrode is in a polygonal ring shape, a quantity of first electrodes is the same as a quantity of edges of the ring electrode, and the plurality of first electrodes each correspond to one edge of the ring electrode.

13. The beauty instrument according to claim 1, wherein the ring electrode is in a polygonal ring shape, and at least a part of the plurality of first electrodes are in a one-to-one correspondence with edges of the ring electrode; and/or the ring electrode is in a polygonal ring shape, and the plurality of first electrodes are in a one-to-one correspondence with at least a part of edges of the ring electrode.

* * * * *